US011583553B2

(12) United States Patent
Oldenburg et al.

(10) Patent No.: US 11,583,553 B2
(45) Date of Patent: Feb. 21, 2023

(54) SILVER NANOPLATE COMPOSITIONS AND METHODS

(71) Applicants: nanoComposix, Inc., San Diego, CA (US); Sebacia, Inc., Duluth, GA (US)

(72) Inventors: Steven J. Oldenburg, San Diego, CA (US); Martin Miranda, San Diego, CA (US); David S. Sebba, Cary, NC (US); Todd J. Harris, Carlsbad, CA (US)

(73) Assignees: NANOCOMPOSIX, LLC, San Diego, CA (US); CORONADO AESTHETICS, LLC, Southlake, TX (US)

( * ) Notice: Subject to any disclaimer, the term of this patent is extended or adjusted under 35 U.S.C. 154(b) by 224 days.

(21) Appl. No.: 16/902,455

(22) Filed: Jun. 16, 2020

(65) Prior Publication Data

US 2020/0306294 A1 Oct. 1, 2020

Related U.S. Application Data

(63) Continuation of application No. 15/374,942, filed on Dec. 9, 2016, now Pat. No. 10,688,126, which is a continuation of application No. 14/947,508, filed on Nov. 20, 2015, now Pat. No. 9,526,745, which is a continuation of application No. 14/681,379, filed on Apr. 8, 2015, now Pat. No. 9,212,294, which is a continuation of application No. PCT/US2013/063920, filed on Oct. 8, 2013.

(Continued)

(51) Int. Cl.
| | |
|---|---|
| B22F 1/14 | (2022.01) |
| A61K 33/38 | (2006.01) |
| A61K 9/51 | (2006.01) |
| A61L 27/00 | (2006.01) |
| B22F 1/16 | (2022.01) |
| B22F 1/145 | (2022.01) |
| B22F 1/0545 | (2022.01) |

(Continued)

(52) U.S. Cl.
CPC ............ *A61K 33/38* (2013.01); *A61K 9/5115* (2013.01); *A61K 9/5123* (2013.01); *A61K 9/5138* (2013.01); *A61K 47/24* (2013.01); *A61K 47/32* (2013.01); *A61L 27/00* (2013.01); *B22F 1/0545* (2022.01); *B22F 1/14* (2022.01); *B22F 1/145* (2022.01); *B22F 1/16* (2022.01); *C08J 3/2053* (2013.01); *C08K 3/08* (2013.01); *C08K 3/28* (2013.01); *C08K 3/36* (2013.01); *C08K 3/38* (2013.01); *C08K 5/092* (2013.01); *C08K 5/1535* (2013.01); *C09D 125/06* (2013.01); *C09D 129/04* (2013.01); *C09D 139/06* (2013.01); *A61L 2300/104* (2013.01); *B22F 1/0551* (2022.01); *B22F 1/068* (2022.01); *B22F 1/147* (2022.01); *B22F 2301/255* (2013.01); *B22F 2998/10* (2013.01); *C08J 2325/18* (2013.01); *C08J 2329/04* (2013.01); *C08K 2003/0806* (2013.01)

(58) Field of Classification Search
CPC .... A61K 33/38; A61K 9/5115; A61K 9/5123; A61K 9/5138; A61K 47/24; A61K 47/32; A61K 9/5107; A61K 47/02; A61K 47/06; A61K 47/36; B22F 1/0545; B22F 1/14; B22F 1/145; B22F 1/16; B22F 1/0551; B22F 1/068; B22F 1/147; B22F 2301/255; B22F 2998/10; A61L 27/00; A61L 2300/104; A61L 27/20; A61L 27/24; A61L 27/36; A61L 27/58; C08J 3/2053; C08J 2325/18; C08J 2329/04; C08K 3/28; C08K 3/08; C08K 3/38; C08K 5/092; C08K 5/1535; C08K 2003/0806; C09D 125/06; C09D 129/04; C09D 139/06; A61P 17/00; A61P 17/06; A61P 17/08; A61P 17/10; A61P 17/12; A61P 17/14; A61P 29/00; A61P 31/04; A61P 31/10; A61P 35/00; C01G 5/00
USPC ......................................................... 523/216
See application file for complete search history.

(56) References Cited

U.S. PATENT DOCUMENTS

| | | |
|---|---|---|
| 1,112,325 A | 9/1914 | Roberts |
| 1,167,462 A | 1/1916 | Wilson |
| (Continued) | | |

FOREIGN PATENT DOCUMENTS

| | | |
|---|---|---|
| WO | 1995033518 | 12/1995 |
| WO | 199620698 | 12/1996 |
| (Continued) | | |

OTHER PUBLICATIONS

Aherne, et al. "Optical Properties and Growth Aspects of Silver Nanoprisms Produced by Highly Reproducible and Rapid Synthesis at Room Temperature." Advanced Materials, Adv. Funct. Mater. Jul. 9, 2008, v18, 2005-2016.

(Continued)

*Primary Examiner* — Hannah J Pak
(74) *Attorney, Agent, or Firm* — Edwin S. Flores; Daniel J. Chalker; Chalker Flores, LLP

(57) ABSTRACT

Embodiments of the present invention relate to methods for preparing high optical density solutions of nanoparticle, such as nanoplates, silver nanoplates or silver platelet nanoparticles, and to the solutions and substrates prepared by the methods. The process can include the addition of stabilizing agents (e.g., chemical or biological agents bound or otherwise linked to the nanoparticle surface) that stabilize the nanoparticle before, during, and/or after concentration, thereby allowing for the production of a stable, high optical density solution of silver nanoplates. The process can also include increasing the concentration of silver nanoplates within the solution, and thus increasing the solution optical density.

11 Claims, 9 Drawing Sheets

Related U.S. Application Data

(60) Provisional application No. 61/795,149, filed on Oct. 11, 2012.

(51) Int. Cl.

| | |
|---|---|
| *C09D 125/06* | (2006.01) |
| *C09D 129/04* | (2006.01) |
| *C09D 139/06* | (2006.01) |
| *C08K 3/28* | (2006.01) |
| *C08K 3/36* | (2006.01) |
| *C08K 3/38* | (2006.01) |
| *C08K 5/092* | (2006.01) |
| *C08K 5/1535* | (2006.01) |
| *A61K 47/24* | (2006.01) |
| *A61K 47/32* | (2006.01) |
| *C08J 3/205* | (2006.01) |
| *C08K 3/08* | (2006.01) |
| *B22F 1/068* | (2022.01) |
| *B22F 1/054* | (2022.01) |

(56) References Cited

U.S. PATENT DOCUMENTS

| | | |
|---|---|---|
| 1,185,242 A | 5/1916 | Reading |
| 1,201,219 A | 10/1916 | Day |
| 1,208,005 A | 12/1916 | Reed |
| 1,210,600 A | 1/1917 | Clark |
| 1,263,447 A | 4/1918 | Mcconnel |
| 1,267,747 A | 5/1918 | Comerma |
| 1,267,801 A | 5/1918 | Pfanstiehl |
| 1,317,245 A | 9/1919 | Townsend |
| 1,325,730 A | 12/1919 | Lyon |
| 1,502,574 A | 7/1924 | Kylin |
| 1,506,763 A | 9/1924 | Mattman |
| 1,506,764 A | 9/1924 | May |
| 1,506,765 A | 9/1924 | Merrill |
| 1,506,766 A | 9/1924 | Mccullough |
| 1,529,513 A | 3/1925 | Swan |
| 1,559,393 A | 10/1925 | Whittelsey |
| 1,559,394 A | 10/1925 | Williams |
| 1,677,843 A | 7/1928 | Parkin |
| 1,744,789 A | 1/1930 | Miller |
| 1,768,749 A | 7/1930 | De Vito |
| 1,861,465 A | 6/1932 | Woodson |
| 1,959,914 A | 5/1934 | George |
| 2,231,283 A | 2/1941 | Pfister |
| 2,343,047 A | 2/1944 | Doyle |
| 2,396,010 A | 3/1946 | Isenberg |
| 2,416,752 A | 3/1947 | Hendrick |
| 3,905,167 A | 9/1975 | Watkins et al. |
| 4,344,141 A | 8/1982 | Yates |
| 4,526,698 A | 7/1985 | Kuroda et al. |
| 5,226,907 A | 7/1993 | Tankovich |
| 5,385,729 A | 1/1995 | Prencipe et al. |
| 5,409,797 A | 4/1995 | Hosoi et al. |
| 5,423,337 A | 6/1995 | Ahlert et al. |
| 5,423,803 A | 6/1995 | Tankovich et al. |
| 5,425,728 A | 6/1995 | Tankovich |
| 5,553,630 A | 9/1996 | Dupuis et al. |
| 5,562,643 A | 10/1996 | Johnson |
| 5,593,680 A | 1/1997 | Bara et al. |
| 5,647,866 A | 7/1997 | Zaias et al. |
| 5,655,547 A | 8/1997 | Kami |
| 5,695,747 A | 12/1997 | Forestier et al. |
| 5,713,845 A | 2/1998 | Tankovich |
| 5,750,120 A | 5/1998 | Miguel-Colombel |
| 5,752,949 A | 5/1998 | Tankovich et al. |
| 5,756,110 A | 5/1998 | Allard et al. |
| 5,759,767 A | 6/1998 | Lakowicz et al. |
| 5,776,440 A | 7/1998 | Forestier et al. |
| 5,810,801 A | 9/1998 | Anderson et al. |
| 5,814,311 A | 9/1998 | Le Bras-Roulier et al. |
| 5,817,089 A | 10/1998 | Tankovich et al. |
| 5,830,177 A | 11/1998 | Li et al. |
| 5,858,381 A | 1/1999 | Le Bras et al. |
| 5,863,522 A | 1/1999 | Forestier et al. |
| 5,925,035 A | 7/1999 | Tankovich |
| 5,955,091 A | 9/1999 | Hansenne |
| 5,958,389 A | 9/1999 | Le Bras-Roulier et al. |
| 5,985,300 A | 11/1999 | Crotty et al. |
| 6,004,567 A | 12/1999 | Marchi-Lemann et al. |
| 6,036,684 A | 3/2000 | Tankovich et al. |
| 6,050,990 A | 4/2000 | Tankovich et al. |
| 6,060,041 A | 5/2000 | Candau et al. |
| 6,063,074 A | 5/2000 | Tankovich |
| 6,080,127 A | 6/2000 | Li et al. |
| 6,132,392 A | 10/2000 | Stone |
| 6,132,745 A | 10/2000 | Marchi-Lemann et al. |
| 6,147,982 A | 11/2000 | Sourour et al. |
| 6,152,917 A | 11/2000 | Tankovich |
| 6,165,440 A | 12/2000 | Esenaliev |
| 6,168,590 B1 | 1/2001 | Neev |
| 6,183,728 B1 | 2/2001 | Forestier et al. |
| 6,183,773 B1 | 2/2001 | Anderson |
| 6,235,270 B1 | 5/2001 | Ishii et al. |
| 6,238,650 B1 | 5/2001 | Lapidot et al. |
| 6,267,771 B1 | 7/2001 | Tankovich et al. |
| 6,283,956 B1 | 9/2001 | McDaniel |
| 6,287,549 B1 | 9/2001 | Sumian et al. |
| 6,333,026 B1 | 12/2001 | Lemann |
| 6,344,050 B1 | 2/2002 | Chen |
| 6,344,272 B1 | 2/2002 | Oldenburg et al. |
| 6,355,054 B1 | 3/2002 | Neuberger |
| 6,365,145 B1 | 4/2002 | Ben-Hur et al. |
| 6,403,653 B1 | 6/2002 | Hobson et al. |
| 6,410,603 B1 | 6/2002 | Hobson et al. |
| 6,428,811 B1 | 8/2002 | West et al. |
| 6,461,595 B1 | 10/2002 | Leo et al. |
| 6,491,929 B1 | 12/2002 | Anderson |
| 6,517,820 B1 | 2/2003 | Robert |
| 6,521,241 B1 | 2/2003 | Minerath, III et al. |
| 6,530,944 B2 | 3/2003 | West et al. |
| 6,534,044 B1 | 3/2003 | Wada et al. |
| 6,541,017 B1 | 4/2003 | Lemann et al. |
| 6,589,538 B1 | 7/2003 | Lemann et al. |
| 6,600,951 B1 | 7/2003 | Anderson |
| 6,611,707 B1 | 8/2003 | Prausnitz et al. |
| 6,620,407 B1 | 9/2003 | Gers-Barlag et al. |
| 6,645,517 B2 | 11/2003 | West et al. |
| 6,660,381 B2 | 12/2003 | Halas et al. |
| 6,663,658 B1 | 12/2003 | Kollias et al. |
| 6,676,655 B2 | 1/2004 | McDaniel |
| 6,685,730 B2 | 2/2004 | West et al. |
| 6,685,927 B2 | 2/2004 | Sumian et al. |
| 6,685,986 B2 | 2/2004 | Oldenburg et al. |
| 6,692,755 B2 | 2/2004 | Gers-Barlag et al. |
| 6,699,724 B1 | 3/2004 | West et al. |
| 6,706,032 B2 | 3/2004 | Weaver et al. |
| 6,720,006 B2 | 4/2004 | Hanke et al. |
| 6,767,547 B2 | 7/2004 | Gers-Barlag et al. |
| 6,793,913 B2 | 9/2004 | Tournilhac et al. |
| 6,800,122 B2 | 10/2004 | Anderson et al. |
| 6,803,049 B2 | 10/2004 | Gers-Barlag et al. |
| 6,811,770 B2 | 11/2004 | Ferrari et al. |
| 6,814,760 B2 | 11/2004 | Anderson et al. |
| 6,821,509 B2 | 11/2004 | Soane et al. |
| 6,838,088 B2 | 1/2005 | Gers-Barlag et al. |
| 6,852,252 B2 | 2/2005 | Halas et al. |
| 6,881,249 B2 | 4/2005 | Anderson et al. |
| 6,887,260 B1 | 5/2005 | McDaniel |
| 6,897,238 B2 | 5/2005 | Anderson |
| 6,942,878 B2 | 9/2005 | Ishii et al. |
| 6,955,639 B2 | 10/2005 | Hainfeld et al. |
| 6,989,151 B2 | 1/2006 | Gers-Barlag et al. |
| 7,008,647 B2 | 3/2006 | Burrell et al. |
| 7,018,396 B2 | 3/2006 | Sierra et al. |
| 7,037,513 B1 | 5/2006 | Traynor et al. |
| 7,081,128 B2 | 7/2006 | Hart et al. |
| 7,131,446 B2 | 11/2006 | Tang et al. |
| 7,144,627 B2 | 12/2006 | Halas et al. |
| 7,201,765 B2 | 4/2007 | McDaniel |
| 7,270,721 B2 | 9/2007 | Hilfenhaus et al. |

(56) References Cited

U.S. PATENT DOCUMENTS

| | | |
|---|---|---|
| 7,328,708 B2 | 2/2008 | Malak |
| 7,367,934 B2 | 5/2008 | Hainfeld et al. |
| 7,371,457 B2 | 5/2008 | Oldenburg et al. |
| 7,435,524 B2 | 10/2008 | Anderson et al. |
| 7,462,496 B2 | 12/2008 | Malak |
| 7,492,458 B2 | 2/2009 | Malak |
| 7,494,503 B2 | 2/2009 | McDaniel |
| 7,530,940 B2 | 5/2009 | Hainfeld et al. |
| 7,648,595 B2 | 1/2010 | Jin et al. |
| 7,659,301 B2 | 2/2010 | Anderson et al. |
| 7,704,754 B2 | 4/2010 | Malak |
| 7,758,561 B2 | 7/2010 | Eppstein |
| 7,758,888 B2 | 7/2010 | Lapidot et al. |
| 7,776,130 B2 | 8/2010 | Mirkin et al. |
| 7,780,955 B2 | 8/2010 | Cassin |
| 7,785,623 B2 | 8/2010 | Keller |
| 7,790,066 B2 | 9/2010 | Wang et al. |
| 7,829,073 B2 | 11/2010 | Martin et al. |
| 7,959,624 B2 | 6/2011 | Riesinger |
| 8,033,977 B2 | 10/2011 | Hainfeld et al. |
| 8,057,418 B2 | 11/2011 | Korbling et al. |
| 8,062,701 B2 | 11/2011 | McClure et al. |
| 8,118,032 B2 | 2/2012 | Malak |
| 8,178,202 B2 | 5/2012 | Halas et al. |
| 8,182,786 B2 | 5/2012 | OBrien et al. |
| 8,197,471 B1 | 6/2012 | Tersigni |
| 8,268,332 B2 | 9/2012 | Manstein |
| 8,268,638 B2 | 9/2012 | Stein et al. |
| 8,285,391 B2 | 10/2012 | Malak |
| 8,377,427 B2 | 2/2013 | Giroud et al. |
| 8,420,062 B2 | 4/2013 | Josso |
| 8,518,445 B2 | 8/2013 | Alfano et al. |
| 8,591,924 B2 | 11/2013 | Zheng |
| 8,613,913 B2 | 12/2013 | Chang et al. |
| 8,617,580 B2 | 12/2013 | Toledano et al. |
| 8,652,495 B2 | 2/2014 | Porter et al. |
| 8,802,154 B2 | 8/2014 | Harris et al. |
| 8,821,940 B2 | 9/2014 | Harris et al. |
| 8,821,941 B2 | 9/2014 | Harris et al. |
| 8,834,447 B2 | 9/2014 | Chen et al. |
| 8,834,933 B2 | 9/2014 | Harris et al. |
| 8,871,711 B2 | 10/2014 | Cotsarelis et al. |
| 8,895,071 B1 | 11/2014 | Harris et al. |
| 8,906,418 B1 | 12/2014 | Harris et al. |
| 8,961,450 B2 | 2/2015 | Anderson et al. |
| 9,061,056 B2 | 6/2015 | Harris et al. |
| 9,212,294 B2 | 12/2015 | Oldenburg et al. |
| 9,249,334 B2 * | 2/2016 | Oldenburg ............ A61P 17/06 |
| 9,421,259 B2 | 8/2016 | Harris et al. |
| 9,421,260 B2 | 8/2016 | Harris et al. |
| 9,421,261 B2 | 8/2016 | Harris et al. |
| 9,427,467 B2 | 8/2016 | Harris et al. |
| 9,433,676 B2 | 9/2016 | Harris et al. |
| 9,433,677 B2 | 9/2016 | Harris et al. |
| 9,433,678 B2 | 9/2016 | Harris et al. |
| 9,439,964 B2 | 9/2016 | Harris et al. |
| 9,439,965 B2 | 9/2016 | Harris et al. |
| 9,446,126 B2 | 9/2016 | Harris et al. |
| 9,572,880 B2 | 2/2017 | Harris et al. |
| 10,342,258 B2 | 7/2019 | Matsumoto et al. |
| 10,351,611 B2 | 7/2019 | Lai et al. |
| 10,688,126 B2 * | 6/2020 | Oldenburg ........... A61K 9/5115 |
| 2001/0002275 A1 | 5/2001 | Oldenburg et al. |
| 2002/0009488 A1 | 1/2002 | Francis et al. |
| 2002/0034480 A1 | 3/2002 | Grimm et al. |
| 2002/0041854 A1 | 4/2002 | Hadasch |
| 2002/0061363 A1 | 5/2002 | Halas |
| 2002/0103517 A1 | 8/2002 | West |
| 2002/0132045 A1 | 9/2002 | Halas |
| 2002/0187172 A1 | 12/2002 | Reb et al. |
| 2002/0192298 A1 | 12/2002 | Burrell et al. |
| 2003/0060811 A1 | 3/2003 | McDaniel |
| 2003/0072728 A1 | 4/2003 | Soane et al. |
| 2003/0095941 A1 | 5/2003 | Anderson |
| 2003/0099718 A1 | 5/2003 | Burrell et al. |
| 2003/0118657 A1 | 6/2003 | West et al. |
| 2003/0156991 A1 | 8/2003 | Halas et al. |
| 2003/0167080 A1 | 9/2003 | Hart et al. |
| 2003/0170189 A1 | 9/2003 | Victor |
| 2003/0215638 A1 | 11/2003 | Charnay et al. |
| 2004/0006328 A1 | 1/2004 | Anderson |
| 2004/0151673 A1 | 8/2004 | Josso |
| 2004/0157237 A1 | 8/2004 | Malak et al. |
| 2004/0166508 A1 | 8/2004 | Pawlak et al. |
| 2004/0170579 A1 | 9/2004 | Mobius |
| 2004/0197286 A1 | 10/2004 | Robert et al. |
| 2004/0219179 A1 | 11/2004 | McDaniel |
| 2004/0253138 A1 | 12/2004 | Malak |
| 2004/0253757 A1 | 12/2004 | Gourlaouen et al. |
| 2005/0031655 A1 | 2/2005 | Karpov |
| 2005/0031658 A1 | 2/2005 | Girier Dufournier et al. |
| 2005/0037034 A1 | 2/2005 | Rhoades |
| 2005/0044642 A1 | 3/2005 | Butcher |
| 2005/0048546 A1 | 3/2005 | Penn et al. |
| 2005/0049582 A1 | 3/2005 | DeBenedictis et al. |
| 2005/0053629 A1 | 3/2005 | Ueda et al. |
| 2005/0058672 A1 | 3/2005 | Gupta |
| 2005/0058678 A1 | 3/2005 | Ricard et al. |
| 2005/0059030 A1 | 3/2005 | Bao et al. |
| 2005/0130324 A1 | 6/2005 | West et al. |
| 2005/0137656 A1 | 6/2005 | Malak |
| 2005/0142605 A1 | 6/2005 | Malak |
| 2005/0146724 A1 | 7/2005 | Malak |
| 2005/0164169 A1 | 7/2005 | Malak |
| 2005/0169866 A1 | 8/2005 | Hannich et al. |
| 2005/0175649 A1 | 8/2005 | Disalvo et al. |
| 2005/0177093 A1 | 8/2005 | Barry et al. |
| 2005/0186235 A1 | 8/2005 | Martin et al. |
| 2005/0186565 A1 | 8/2005 | Malak |
| 2005/0187128 A1 | 8/2005 | Martin et al. |
| 2005/0203495 A1 | 9/2005 | Malak |
| 2005/0220741 A1 | 10/2005 | Dumousseaux |
| 2005/0229334 A1 | 10/2005 | Huang et al. |
| 2005/0256554 A1 | 11/2005 | Malak |
| 2005/0283145 A1 | 12/2005 | Malak |
| 2006/0078578 A1 | 4/2006 | Sandewicz et al. |
| 2006/0083762 A1 | 4/2006 | Brun et al. |
| 2006/0257336 A1 | 11/2006 | Ferrari et al. |
| 2007/0032781 A1 | 2/2007 | Henry et al. |
| 2007/0065387 A1 | 3/2007 | Beck et al. |
| 2007/0078290 A1 | 4/2007 | Esenaliev |
| 2007/0092471 A1 | 4/2007 | Cassier et al. |
| 2007/0104605 A1 | 5/2007 | Hampden-Smith et al. |
| 2007/0125383 A1 | 6/2007 | Ko |
| 2007/0154903 A1 | 7/2007 | Marla et al. |
| 2007/0158611 A1 | 7/2007 | Oldenburg |
| 2007/0160636 A1 | 7/2007 | Kasai |
| 2007/0160896 A1 | 7/2007 | Malak et al. |
| 2007/0166248 A1 | 7/2007 | L'Alloret et al. |
| 2007/0183992 A1 | 8/2007 | Dumousseaux et al. |
| 2007/0196305 A1 | 8/2007 | Wang et al. |
| 2007/0208400 A1 | 9/2007 | Nadkarni et al. |
| 2007/0217996 A1 | 9/2007 | Levy et al. |
| 2007/0231940 A1 | 10/2007 | Gourlaouen et al. |
| 2008/0004173 A1 | 1/2008 | Miura et al. |
| 2008/0045865 A1 | 2/2008 | Kislev |
| 2008/0050448 A1 | 2/2008 | Wilson et al. |
| 2008/0077203 A1 | 3/2008 | Malak |
| 2008/0188558 A1 | 8/2008 | Godal et al. |
| 2008/0204742 A1 | 8/2008 | Halas et al. |
| 2008/0208179 A1 | 8/2008 | Chan et al. |
| 2008/0214988 A1 | 9/2008 | Altshuler et al. |
| 2008/0233060 A1 | 9/2008 | Grune |
| 2008/0234535 A1 | 9/2008 | Malak et al. |
| 2008/0241262 A1 | 10/2008 | Lee et al. |
| 2008/0248001 A1 | 10/2008 | Bourke |
| 2008/0288007 A1 | 11/2008 | Malak |
| 2008/0294116 A1 | 11/2008 | Wolter et al. |
| 2008/0305337 A1 | 12/2008 | Berning et al. |
| 2009/0012445 A1 | 1/2009 | Malak |
| 2009/0022765 A1 | 1/2009 | Chung et al. |
| 2009/0022766 A1 | 1/2009 | Geddes |
| 2009/0053268 A1 | 2/2009 | DePablo et al. |
| 2009/0071168 A1 | 3/2009 | Malak |

(56) References Cited

U.S. PATENT DOCUMENTS

| | | |
|---|---|---|
| 2009/0123509 A1 | 5/2009 | Berkland et al. |
| 2009/0130445 A1 | 5/2009 | Malak |
| 2009/0175915 A1 | 7/2009 | Maitra et al. |
| 2009/0177122 A1 | 7/2009 | Peterson |
| 2009/0217465 A1 | 9/2009 | Cremer et al. |
| 2009/0226521 A1 | 9/2009 | Smyth et al. |
| 2009/0246142 A1 | 10/2009 | Bhatia et al. |
| 2009/0291107 A1 | 11/2009 | Schehlmann et al. |
| 2009/0326358 A1 | 12/2009 | Malak |
| 2009/0326614 A1 | 12/2009 | El-Sayed et al. |
| 2010/0002282 A1 | 1/2010 | Agrawal et al. |
| 2010/0016782 A1 | 1/2010 | Oblong |
| 2010/0016783 A1 | 1/2010 | Bourke, Jr. et al. |
| 2010/0040549 A1 | 2/2010 | Halas et al. |
| 2010/0049178 A1 | 2/2010 | Deem et al. |
| 2010/0055138 A1 | 3/2010 | Margulies et al. |
| 2010/0056485 A1 | 3/2010 | Park |
| 2010/0057068 A1 | 3/2010 | Lee |
| 2010/0104652 A1 | 4/2010 | Biris et al. |
| 2010/0119610 A1 | 5/2010 | Schoen et al. |
| 2010/0143431 A1 | 6/2010 | Landau et al. |
| 2010/0172994 A1 | 7/2010 | Sigmund et al. |
| 2010/0174223 A1 | 7/2010 | Sakamoto et al. |
| 2010/0204686 A1 | 8/2010 | Yaroslavksy et al. |
| 2010/0224026 A1 | 9/2010 | Foumet et al. |
| 2010/0233222 A1 | 9/2010 | Girier Dufournier et al. |
| 2010/0254920 A1 | 10/2010 | LAlloret et al. |
| 2010/0260700 A1 | 10/2010 | Dop |
| 2010/0266647 A1 | 10/2010 | Dingley et al. |
| 2010/0266649 A1 | 10/2010 | Maitra et al. |
| 2010/0272789 A1 | 10/2010 | Satoh et al. |
| 2010/0284924 A1 | 11/2010 | Zink et al. |
| 2010/0291166 A1 | 11/2010 | Guyot-Ferreol et al. |
| 2010/0291224 A1 | 11/2010 | Tong et al. |
| 2010/0298758 A1 | 11/2010 | Christiansen et al. |
| 2010/0303716 A1 | 12/2010 | Jin et al. |
| 2010/0305495 A1 | 12/2010 | Anderson et al. |
| 2010/0323996 A1 | 12/2010 | Ute et al. |
| 2011/0021970 A1 | 1/2011 | Vo-Dinh et al. |
| 2011/0034855 A1 | 2/2011 | Esenaliev |
| 2011/0052672 A1 | 3/2011 | Krishnan et al. |
| 2011/0091572 A1 | 4/2011 | Davidson |
| 2011/0097285 A1 | 4/2011 | Malak |
| 2011/0111002 A1 | 5/2011 | Pop |
| 2011/0117202 A1 | 5/2011 | Bourke, Jr. et al. |
| 2011/0144030 A1 | 6/2011 | Ramis Castelltort et al. |
| 2011/0159291 A1 | 6/2011 | Sun et al. |
| 2011/0168200 A1 | 7/2011 | Bourdin et al. |
| 2011/0223255 A1 | 9/2011 | Thiesen et al. |
| 2011/0229559 A1 | 9/2011 | Prestidge et al. |
| 2011/0240556 A1 | 10/2011 | Hoek et al. |
| 2011/0288234 A1 | 11/2011 | Pandey et al. |
| 2011/0306955 A1 | 12/2011 | Thorhauge et al. |
| 2012/0021030 A1 | 1/2012 | Matsufuji et al. |
| 2012/0059307 A1 | 3/2012 | Harris et al. |
| 2012/0101007 A1 | 4/2012 | Ahem et al. |
| 2012/0141380 A1 | 6/2012 | Margel et al. |
| 2012/0283328 A1 | 11/2012 | Modi |
| 2012/0289955 A1 | 11/2012 | Marc |
| 2013/0017238 A1 | 1/2013 | Porter et al. |
| 2013/0022655 A1 | 1/2013 | Sachweh et al. |
| 2013/0023714 A1 | 1/2013 | Johnston et al. |
| 2013/0183244 A1 | 7/2013 | Hanes et al. |
| 2013/0195979 A1 | 8/2013 | Tersigni |
| 2013/0216596 A1 | 8/2013 | Viladot Petit et al. |
| 2013/0225901 A1 | 8/2013 | Krishnan et al. |
| 2013/0251825 A1 | 9/2013 | Berry |
| 2013/0315650 A1 | 11/2013 | Cassin et al. |
| 2013/0315999 A1 | 11/2013 | Paithankar et al. |
| 2013/0323305 A1 | 12/2013 | Paithankar et al. |
| 2013/0338545 A1 | 12/2013 | Azhari et al. |
| 2014/0005593 A1 | 1/2014 | Harris et al. |
| 2014/0012162 A1 | 1/2014 | Harris et al. |
| 2014/0012163 A1 | 1/2014 | Harris et al. |
| 2014/0012183 A1 | 1/2014 | Harris et al. |
| 2014/0030300 A1 | 1/2014 | Maitra et al. |
| 2014/0105982 A1 | 4/2014 | Oldenburg et al. |
| 2014/0120041 A1 | 5/2014 | Prencipe et al. |
| 2014/0120167 A1 | 5/2014 | Lapotko et al. |
| 2014/0120168 A1 | 5/2014 | Oldenburg et al. |
| 2014/0194900 A1 | 7/2014 | Sedic |
| 2014/0205546 A1 | 7/2014 | Macoviak |
| 2014/0206712 A1 | 7/2014 | Gant et al. |
| 2014/0243934 A1 | 8/2014 | Vo-Dinh et al. |
| 2014/0271889 A1 | 9/2014 | Messersmith et al. |
| 2014/0303525 A1 | 10/2014 | Sitharaman |
| 2014/0316387 A1 | 10/2014 | Harris et al. |
| 2014/0316394 A1 | 10/2014 | Quidant et al. |
| 2014/0371654 A1 | 12/2014 | Harris et al. |
| 2014/0371655 A1 | 12/2014 | Harris et al. |
| 2014/0371656 A1 | 12/2014 | Harris et al. |
| 2014/0371658 A1 | 12/2014 | Harris et al. |
| 2014/0371659 A1 | 12/2014 | Harris et al. |
| 2014/0371661 A1 | 12/2014 | Harris et al. |
| 2014/0371662 A1 | 12/2014 | Harris et al. |
| 2014/0371663 A1 | 12/2014 | Harris et al. |
| 2014/0371664 A1 | 12/2014 | Harris et al. |
| 2015/0005691 A1 | 1/2015 | Harris et al. |
| 2015/0045723 A1 | 2/2015 | Paithankar et al. |
| 2015/0165180 A1 | 6/2015 | Anderson et al. |
| 2015/0190341 A1 | 7/2015 | Paithankar et al. |
| 2015/0196359 A1 | 7/2015 | Paithankar |
| 2015/0196452 A1 | 7/2015 | Meyer et al. |
| 2015/0196639 A1 | 7/2015 | Lando et al. |
| 2015/0225599 A1 | 8/2015 | Oldenburg et al. |
| 2016/0287741 A1 | 10/2016 | Harris et al. |
| 2016/0310527 A1 | 10/2016 | Paithankar et al. |
| 2018/0325594 A1 | 11/2018 | Paithankar |

FOREIGN PATENT DOCUMENTS

| | | |
|---|---|---|
| WO | 1996041579 | 12/1996 |
| WO | 199822031 | 1/1997 |
| WO | 199824507 | 1/1997 |
| WO | 199946351 | 1/1997 |
| WO | 200002590 | 1/1997 |
| WO | 1997000098 | 1/1997 |
| WO | 9822031 A1 | 5/1998 |
| WO | 200105586 | 7/2000 |
| WO | 200106257 | 7/2000 |
| WO | 200158458 | 7/2000 |
| WO | 2000040266 A2 | 7/2000 |
| WO | 2002085385 | 10/2002 |
| WO | 03026600 A1 | 4/2003 |
| WO | 1991006894 | 4/2003 |
| WO | 2003026481 | 4/2003 |
| WO | 2004058352 A2 | 7/2004 |
| WO | 2004086044 A1 | 10/2004 |
| WO | 2005046793 A2 | 5/2005 |
| WO | 2005077329 A1 | 8/2005 |
| WO | 2005092286 A2 | 10/2005 |
| WO | 2006051542 A1 | 5/2006 |
| WO | 2006122222 A2 | 11/2006 |
| WO | 2008079758 A1 | 7/2008 |
| WO | 2008079760 A2 | 7/2008 |
| WO | 2008079898 A1 | 7/2008 |
| WO | 2008106966 A1 | 9/2008 |
| WO | 2009061349 A1 | 5/2009 |
| WO | 2009117124 A1 | 9/2009 |
| WO | 2009124189 A1 | 10/2009 |
| WO | 2009130689 A2 | 10/2009 |
| WO | 2010073260 A1 | 7/2010 |
| WO | 2010109545 A1 | 9/2010 |
| WO | 2010116345 A1 | 10/2010 |
| WO | 2010116346 A1 | 10/2010 |
| WO | 2010137580 A1 | 12/2010 |
| WO | 2010144257 A1 | 12/2010 |
| WO | 2011013101 A1 | 2/2011 |
| WO | 2011031871 A1 | 3/2011 |
| WO | 2011095970 A1 | 8/2011 |
| WO | 2011116963 A2 | 9/2011 |
| WO | 2012027728 A2 | 3/2012 |
| WO | 2012035029 A2 | 3/2012 |
| WO | 2012059944 A2 | 5/2012 |

(56) References Cited

FOREIGN PATENT DOCUMENTS

| WO | 2013106998 A1 | 7/2013 |
|---|---|---|
| WO | 2013106999 A1 | 7/2013 |
| WO | 2013107000 A1 | 7/2013 |
| WO | 2013107001 A1 | 7/2013 |
| WO | 2013107002 A1 | 7/2013 |
| WO | 2013107349 A1 | 7/2013 |
| WO | 2013107350 A1 | 7/2013 |
| WO | 2013107351 A1 | 7/2013 |
| WO | 2013107352 A1 | 7/2013 |
| WO | 2013107353 A1 | 7/2013 |
| WO | 2013107354 A1 | 7/2013 |
| WO | 2013158278 A1 | 10/2013 |
| WO | 2013160362 A1 | 10/2013 |
| WO | 2013169955 A1 | 11/2013 |
| WO | 2014026142 A1 | 2/2014 |
| WO | 2014052973 A1 | 4/2014 |
| WO | 2014145784 A1 | 9/2014 |
| WO | 2017083819 A1 | 5/2017 |

OTHER PUBLICATIONS

Alexandrite Laser Hair Removal; Journal of the Japan Society of Aesthetic Surgery, v. 36, No. 1, Jan. 1999.

American Society for Laser Medicine and Surgery Abstracts, 32nd ASLMS Annual Conference, Abstract #LB3 at p. 351, titled Selective Photothermolysis of the Sebaceous Follicle with Gold-Coated Nanoshells for the Treatment of Acne; Kauvar, Lloyd, Cheung, Zabinska, Owczarek, Majewski, Farinelli, Anderson, Sakamoto (Abstract #LB3 at p. 351: Wileyonlinelibrary.com, Wiley Periodicals, Inc. Published Apr. 10, 2012).

Amirthalingam et al. "Use of Silica-Gold Core Shell Structure Nanoparticles for Targeted Drug Delivery System" J. Nanomedic Nanotechnol 2:119, (2011) vol. 2, Issue 6.

Ammad et al. "An assessment of the efficacy of blue light phototherapy in the treatment of acne vulgaris." J Cosmet Dermatol, 2008, 7: 180-188.

Bukasov et al. "Nano Letters—Highly tunable infrared extinction properties of gold nanocrescents." American Chemical Society, vol. 7, No. 5 May 2007, published on web Apr. 14, 2007.

Charles et al. "Versatile Solution Phase Triangular Silver Nanoplates for Highly Sensitive Plasmon Resonance Sensing" American Chemical Society NANO, v4, No. 1 p. 55-64, Dec. 23, 2009.

Chen et al. "Controlling 2-dimensional growth of silver nanoplates." Self-Assembled Nanostructured Materials Symposium. Mat. Res. Soc. Symp. Proc. vol. 775, 343-348|xiii+394. (2003).

Chen et al. "Silver nanodisks: Synthesis, characterization, and self-assembly" J. Phys. Chem. B, vol. 106, No. 42, 2002 10777-10781. (Published Sep. 21, 2002).

Chen, et al. "Silver nanoplates: Size control in two dimensions and formation mechanisms." J. Phys. Chem. B 2004, 108, 5500-5506 Journal of Physical Chemistry B, 108, 5500-5506. (Published Apr. 14, 2004).

Chen, et al. "Synthesis and characterization of truncated triangular silver nanoplates." Nano Letters, 2002, 2 (9), 1003-1007. (Published Jul. 26, 2002).

Choudhary and Elsaie, M.L. "Photodynamic therapy in dermatology: a review." Lasers Med Sci., 2009, 24:971-980.

Contrasting Properties of Gold Nanoparticles for Optical Coherence Tomography: Phantom, in vivo studies and Monte Carlo simulation; Zagaynova et al; Phys. Med. Biol. 53 (2008) 499-5009; Published Aug. 18, 2008.

Dierickx, et al. "Photodynamic Therapy for Nevus Sebaceus With Topical d-Aminolevulinic Acid", Arch Dermatol, vol. 135, Jun. 1993, pp. 637-640.

Divaris, et al. "Phototoxic Damage to Sebaceous Glands and Hair Follicles of Mice After Systemic Administration of 5-Aminolevulinic Acid Correlates with Localized Protoporphyrin IX Florescence", American Journal of Pathology, vol. 136, No. 4, Apr. 1990, pp. 891-897.

Donnelly et al. "Photosensitiser delivery for photodynamic therapy. Part 1: Topical carrier platforms." Expert Opin Drug Deliv. 2008, 5:757-766.

Ghaffarpour, Azizjalali M. et al., "CO2 Laser therapy versus cryotherapy in treatment of genital warts; a Randomized Controlled Trial (RCT)", Iranian Journal of Microbiology, vol. 4, No. 4, Dec. 2012, 187-190.

Gollnick et al. "Can we define acne as a chronic disease If so, how and when" Am J Clin Dermatol, 2008, 9:279-284.

Grachtchouk et al. "Basal cell carcinomas in mice arise from hair follicle stem cells and multiple epithelial progenitor populations." J Clin Invest, 2011, 121: 1768-1781.

Grams et al. "Permeant lipophilicity and vehicle composition influence accumulation of dyes in hair follicles of human skin," Eur J Pharm Sci, 2003, 18:329-336.

Hao E. K., et al. "Synthesis of Silver Nanodisks using Polystyrene Mesospheres as Templates." J Am Chem Soc, 124, 15182-15183. (Published Nov. 22, 2002).

Hao E., et al. "Synthesis and optical properties of anisotropic metal nanoparticles." Journal of Fluorescence, vol. 14, No. 4, Jul. 2004, 331-341. (Published Jul. 2004).

He et al. "Surface Plasmon Resonances of Silver Triangle Nanoplates: Graphic Assignments of Resonance Modes and Linear Fittings of Resonance Peaks" J. Phys. Chem. B 2005, 109, 17503-17511 (Published Aug. 20, 2005).

He, et al. "The evidence for synthesis of truncated silver nanoplates in the presence of CTAB." Materials Characterization, 59, 380-384. (Published 2008).

Hongcharu, et al. "Topical ALA-Photodynamic Therapy for the Treatment of Acne Vulgaris", Journal of Invest. Dermatology, vol. 115, No. 2, Aug. 2000, pp. 183-192 (10 pages).

Huang et al. Microemulsification of triglyceride sebum and the role of interfacial structure on bicontinuous phase behavior.: Langmuir, 2004, 20:3559-3563.

Jiang et al. "A self-seeding coreduction method for shape control of silver nanoplates" Nanotechnology 17 (2006) 4929-4935 (Published Sep. 11, 2006).

Jin et al. "Photoinduced Conversion of Silver Nanospheres to Nanoprisms." Science, v 294, 1901-1903. (Published Nov. 30, 2001).

Jin, et al. "Controlling anisotropic nanoparticle growth through plasmon excitation." Nature, v. 425, 487-490 (Published Oct. 2, 2003).

Kjeldstad, et al. "Changes in Polyphosphate Composition and Localization in Propionibacterium Acnes After Near-Ultraviolet Irradiation", Canadian Journal of Microbiology, vol. 37, No. 7, Jul. 1991, 562-567 (Abstract, 1 Page).

Knorr et al. "Follicular transport route-research progress and future perspectives." Eur J Pharm Biopharm, 2009, 71:173-180.

Koenig, et al. "Photodynamic-Induced Inactivation of Propionibacterium Acnes", SPIE Proceedings, SPIE-Int. Soc. Opt Eng., 106-110, vol. 3247, Jan. 1998 (Abstract, 3 Pages).

Konig, et al. "Photodynamic Activity of Methylene Blue", Aktuelle Dermatol, vol. 19, 1993, pp. 195-198.

Konig, et al. "Photodynamically Induced Inactivation of Propionibacterium Acnes Using the Photosensitizer Methylene Blue and Red Light", Dermatologische Monatsschrift (Dermatol Monatsschr), vol. 178, Apr. 1992, pp. 297-300.

Kulkarni et al., "Effect of Experimental Temperature on the Permeation of Model Diffusants Across Porcine Buccal Mucosa" AAPS PharmSciTech. Jun. 2011; 12(2)579.

Lademann et al. "Nanoparticles—an efficient carrier for drug delivery into the hair follicles." Eur J Pharm Biopharm, 2007, 66:159-164.

Lazare, M. What are Cold Sores (Herpetic Lesions), http://www.drmarclazare.com/laser-treatments-for-cold-soresherpetic-lesio- ns/, dated Jul. 8, 2014.

Le Guevel, et al. "Synthesis, Stabilization, and Functionalization of Silver Nanoplates for Biosensor Applications." J Phys Chem C, 113, 16380-16386. (Published Aug. 21, 2009).

Lewicka et al. "Nanorings and nanocrescents formed via shaped nanosphere lithography: a route toward large areas of infrared metamaterials." IOP Publishing, Nanotechnology 24: Feb. 28, 2013.

(56) References Cited

OTHER PUBLICATIONS

Lloyd, et al. "Selective Photothermolysis of the Sebaceous Glands for Acne Treatment", Lasers in Surgery and Medicine, vol. 31, 2002, pp. 115-120.
Mallon et al. "The quality of life in acne: a comparison with general medical conditions using generic questionnaires." Br J Dermatol, 1999, 140:672-676.
Maltzahn, Geoffrey von, et al., "Computationally Guided Photothermal Tumor Therapy Using Long-Circulating Gold Nanorod Antennas" Cancer Res 2009; 69: (9) Published online Apr. 14, 2009 as 10.11158/008-5472.CAN-08-4242.
Meidan, V.M. "Methods for quantifying intrafollicular drug delivery: a critical appraisal." Expert Opin Drug Deliv, 2010, 7:1095-1108.
Metraux, G. S. M. et al. "Rapid Thermal Synthesis of Silver Nanoprisms with Chemically Tailorable Thickness." Advanced Materials, 2005, 17, No. 4, 412-415. (Published Feb. 23, 2005).
Mills, et al. "Ultraviolet Phototherapy and Photochemotherapy of Acne Vulgaris", Arch Dermatol, vol. 114, No. 2, Feb. 1978 (Abstract, 2 pages).
Mitragotri et al. "Synergistic effect of low-frequency ultrasound and sodium lauryl sulfate on transdermal transport." J Pharm Sci, 2000, 89:892-900.
Mortensen et al. "In vivo skin penetration of quantum dot nanoparticles in the murine model: the effect of UVR." Nano Lett, 2008, 8:2779-2787.
Mutzhas, et al. "A New Apparatus with High Radiation Energy Between 320-460 nm: Physical Description and Dermatological Applications", The Journal of Investigative Dermatology, vol. 76, No. 1, Jan. 1981, pp. 42-47.
Nanni, C.A. and Alster, T.S. (1997). "Optimizing treatment parameters for hair removal using a topical carbon-based solution and 1064-nm Q-switched neodymium: YAG laser energy." Arch Dermatol, 1997, 133:1546-1549.
New Attempts for Treatment by Electrical Incineration; Skin Surgery V. 11, No. 2, Nov. 2002 (Japanese translation).
Pento, et al. "Delta-Aminolevulinic Acid", Drugs of the Future, vol. 22, No. 1, 1997, pp. 11-17.
Phillips, et al. "Medical Progress: Recent Advances in Dermatology", New England Journal Of Medicine, vol. 326, No. 3, Jan. 1992, pp. 1-9 (167-176).
Polat et al. "Ultrasound-mediated transdermal drug delivery: Mechanisms, scope, and emerging trends." J Control Release, 2011, 152:330-348.
Prosecution history of U.S. Appl. No. 13/789,575, including a 37 CFR 1.131 declaration over US Publication 2014/0005593 with U.S. Appl. No. 14/020,481, now U.S. Pat. No. 8,821,941. The 131 declaration is dated Dec. 31, 2014 (submission date to USPTO).
Prosecution history of U.S. Appl. No. 13/789,575, namely an Advisory Action further to a Suggestion for Declaration of Interference over US Publication 2014/0005593 with U.S. Appl. No. 14/020,481, now U.S. Pat. No. 8,821,941. The Advisory Action and related documentation is dated Aug. 21, 2015 (mailing date from USPTO).
Prosecution history of U.S. Appl. No. 13/789,575, namely an Amendment and a Suggestion for Declaration of Interference (with Appendices) over US Publication 2014/0005593 with U.S. Appl. No. 14/020,481, now U.S. Pat. No. 8,821,941 The Amendment and Suggestion for Declaration of Interference (with Appendices) and related documentation is dated Jul. 28, 2015 (submission date to USPTO) (Part 1 of 5).
Prosecution history of U.S. Appl. No. 13/789,575, namely an amendment in view of a Suggestion for Declaration of Interference over US Publication 2014/0005593 with U.S. Appl. No. 14/020,481, now U.S. Pat. No. 8,821,941. The amendment and related documentation is dated Aug. 19, 2015 (submission date to USPTO).
Prosecution history of U.S. Appl. No. 13/789,575, namely Exhibits from a Suggestion for Declaration of Interference over US Publication 2014/0005593 with U.S. Appl. No. 14/020,481, now U.S. Pat. No. 8,821,941. The Exhibits from a Suggestion for Declaration of Interference and related documentation is dated Jul. 28, 2015 (submission date to USPTO) (Part 3 of 5).
Prosecution history of U.S. Appl. No. 13/789,575, namely Exhibits from a Suggestion for Declaration of Interference over US Publication 2014/0005593 with U.S. Appl. No. 14/020,481, now U.S. Pat. No. 8,821,941. The Exhibits from a Suggestion for Declaration of Interference and related documentation is dated Jul. 28, 2015 (submission date to USPTO) (Part 2 of 5).
Prosecution history of U.S. Appl. No. 13/789,575, namely Exhibits from a Suggestion for Declaration of Interference over US Publication 2014/0005593 with U.S. Appl. No. 14/020,481, now U.S. Pat. No. 8,821,941. The Exhibits from a Suggestion for Declaration of Interference and related documentation is dated Jul. 28, 2015 (submission date to USPTO) (Part 4 of 5).
Prosecution history of U.S. Appl. No. 13/789,575, namely Exhibits from a Suggestion for Declaration of Interference over US Publication 2014/0005593 with U.S. Appl. No. 14/020,481, now U.S. Pat. No. 8,821,941. The Exhibits from a Suggestion for Declaration of Interference and related documentation is dated Jul. 28, 2015 (submission date to USPTO) (Part 5 of 5).
Rallis, Tena M., "Low-Intensity Laser Therapy for Recurrent Herpes Labialis" The Journal of Investigative Dermatology, vol. 115, No. 1 Jul. 2000.
Rogers et al. "Hair removal using topical suspension-assisted Q-switched Nd: YAG and long-pulsed alexandrite lasers: A comparative study." Dermatol Surg, 1999, 25:844-844; discussion 848-850.
Rother K. "Diabetes Treatment-Bridging the Divide", N Engl J Med. 356:15, published Apr. 12, 2007.
Sakamoto et al. "Photodynamic therapy for acne vulgaris: A critical review from basics to clinical practice: Part 1, Acne Vulgaris: When and why consider photodynamic therapy" Journal of the American Academy of Dermatology, 2010, 63:183-193. cited by applicant.
Sakamoto et al. "Photodynamic therapy for acne vulgaris: A critical review from basics to clinical practice: Part II. Understanding parameters for acne treatment with photodynamic therapy." Journal of the Academy of Dermatology, 2010, 63:195-211.
Schultz, et al. "The Chemorheology of Poly(vinyl alcohol)-Borate Gels." Macromolecules, vol. 2, No. 3, 281-285. (Published May-Jun. 1969).
Sellheyer, K. "Basal cell carcinoma: cell of origin, cancer stem cell hypothesis and stem cell markers." Br J Dermatol, 2011, 164:696-711.
Sellheyer, K. (2007). "Mechanisms of laser hair removal: could persistent photoepilation induce vitiligo or defects in wound repair" Dermatol Surg, 2007, 33:055-1065.
Shershen et al. "Temperature-Sensitive Polymer—Nanoshell Composites For Photothermally Modulated Drug Delivery" Journal of Biomedical Materials Research; vol. 51, Issue 3, pp. 293-298 (Jun. 28, 2000).
Vogt A et al. "40 nm, but not 750 or 1,500 nm, Nanoparticles Enter Epidermal CD 1a + Cells after Transcutaneous Application on Human Skin", Journal of Investigative Dermatology (2006) 126, 1316-1322, published Apr. 13, 2006.
Wainwright, Mark "Non-Porphyrin Photosensitizers in Biomedicine", Chemical Society Reviews, 1996, pp. 351-359.
West et al. "Applications Of Nanotechnology To Biotechnology" Current Opinion in Biotechnology 2000, 11:215-217; Published Apr. 1, 2000.
Wong, S.Y., and Reiter, J.F. "Wounding mobilizes hair follicle stem cells to form tumors." Proc Natl Acad Sci USA, 2011, 108:4093-4098.
Xiong, et al. "Synthesis of silver nanoplates at high yields by slowing down the polyol reduction of silver nitrate with polyacrylamide." Journal of Materials Chemistry, 17, 2600-2602. (Published May 17, 2007).
Xue, et al. "pH-Switchable Silver Nanoprism Growth Pathways." Angew. Chem. Int. Ed., 46, 2036-2038. (Published Feb. 13, 2007).
Zhao, W., and Karp, J.M. "Tumour targeting: Nanoantennas heat up." Nat Mater, 2009, 8:453-454.

\* cited by examiner

SILVER NANOPLATE COMPOSITIONS AND METHODS

INCORPORATION BY REFERENCE TO ANY PRIORITY APPLICATIONS

This application is a continuation of U.S. application Ser. No. 15/374,942, filed Dec. 9, 2016 and issued as U.S. Pat. No. 10,688,126, which is a continuation of U.S. application Ser. No. 14/947,508, filed Nov. 20, 2015 and issued as U.S. Pat. No. 9,526,745, which is a continuation of U.S. application Ser. No. 14/681,379, filed Apr. 8, 2015 and issued as U.S. Pat. No. 9,212,294, which is a continuation of International Application No. PCT/US2013/063920, filed Oct. 8, 2013 and published in English as WO 2014/058904 on Apr. 17, 2014, which claims the benefit of priority from U.S. Provisional Application 61/795,149, filed on Oct. 11, 2012, each of which is incorporated by reference in its entirety, herein. Any and all applications for which a foreign or domestic priority claim is identified in the Application Data Sheet as filed with the present application are hereby incorporated by reference under 37 CFR 1.57.

PARTIES TO JOINT RESEARCH AGREEMENT

The invention described herein was created subject to a Joint Research Agreement between Sienna Labs, Inc. and nanoComposix, Inc.

BACKGROUND

Field of the Invention

The invention relates to a method for preparing high optical density solutions of silver platelet nanoparticles (e.g., nanoplates) and to nanoparticles, solutions and substrates prepared by said methods.

Description of the Related Art

Nanoparticles, including nanospheres, nanorods, nanowires, nanocubes, nanoplates, as well as other shapes can be synthesized from a range of materials. In one embodiment, a platelet nanoparticle is a nanoplate. Nanoparticles made from metals including gold and silver have unique optical properties which can be tuned to interact with light throughout the electromagnetic spectrum due to the localized surface plasmon resonance supported by these nanomaterials. Technologies that take advantage of the unique optical properties of silver nanoparticles include, but are not limited to, diagnostic, photonic, medical, and obscurant technologies. A subset of these technologies including photothermal tumor ablation, hair removal, acne treatment, wound healing, and antimicrobial applications among others, may use solutions of nanoparticles with high optical densities. Silver nanoplates, which are also known as silver platelet nanoparticles or nanoprisms, are of particular interest for technologies that utilize nanoparticle optical properties due to their tunable spectral peaks and extremely high optical efficiencies. While methods of fabricating silver nanoplates via photoconversion (Jin et al. 2001; Jin et al. 2003); pH-controlled photoconversion (Xue 2007); thermal growth (Hao et al. 2004; Hao 2002; He 2008; Metraux 2005); templated growth (Hao et al. 2004; Hao 2002); and seed mediated growth (Aherne 2008; Chen; Carroll 2003; Chen; Carroll 2002, 2004; Chen et al. 2002; He 2008; Le Guevel 2009; Xiong et al. 2007) have been developed, these methods generate relatively dilute solutions with correspondingly low visible and near-infrared optical density.

SUMMARY

For many silver nanoplate applications, a more concentrated solution of the silver nanoplates is of utility and can be particularly advantageous. In some instances, when as-fabricated solutions of silver nanoplates are concentrated to yield a higher particle density under previously developed methods, the shape of the nanoparticle can undergo a change resulting in a shift in optical properties, such as optical density. In many cases, these changes result in an undesirable degradation of the nanoparticle's optical properties. Accordingly, several embodiments of the present invention provide methods of preparing silver nanoplates solutions in higher concentrations with increased optical density while reducing degradation of the silver nanoplates' optical properties. In various embodiments, methods of the present invention provide for preparing high optical density solutions of silver nanoplates from dilute silver nanoplate solutions that partially, substantially, or fully preserve the shape and optical properties of the fabricated silver nanoplates when the particle concentration is increased.

Various embodiments of the invention provide methods for preparing high optical density solutions of silver nanoplates, as well as the nanoparticles and solutions prepared by those methods. In one embodiment, the process comprises the replacement of one or more original components (e.g., chemical or biological agents) bound to, or otherwise coupled to, the nanoparticle surface with a stabilizing agent. In another embodiment, the stabilizing agent does not replace the original component but rather supplements or alters the original component. The stabilizing agent can be a biological or chemical agent that stabilizes the nanoplates before, during, and/or after concentration, thereby allowing for the production of a stable, high optical density solution of silver nanoplates. In one embodiment, the process also comprises a method of increasing the concentration of silver nanoplates within the solution, and thus increasing the solution optical density. In several embodiments, the stability (e.g., the characteristics of the nanoparticles in the solution, such as shape, size, optical properties, peak response, plasmonic properties, etc.) of the high optical density solution is unaffected or substantially unaffected during the process. Several embodiments of the invention comprise a high optical density solution of silver nanoplates that have been stabilized with stabilizing agents (e.g., surface bound molecules, chemical agents, and/or biological agents). In one embodiment, the invention comprises a solution of silver nanoplates that have been surface functionalized with chemical or biological agents that are physisorbed to the surface, molecularly bound to the surface through specific interactions, or encapsulate each nanoparticle.

In one embodiment, a high optical density solution of silver nanoplates is associated with a substrate. In one embodiment, a portion of the nanoplates in solution bind to the substrate to create a nanoplate-substrate composite. The high optical density solutions of silver nanoplates can be exposed to substrates to generate nanoplate composites where a substantial portion of the surface area of a substrate is coated with nanoplates. In some embodiments the substrate comprises fibers, cloth, mesh, bandages, socks, wraps, other articles of clothing, sponges, high porosity substrates, particles with edge lengths greater than 1 micron, beads, hair, skin, paper, absorbent polymers, foam, wood, cork, slides, roughened surfaces, biocompatible substrates, filters, and/or medical implants.

In several embodiments, a process for increasing the optical density of a stable, silver nanoplate solution, comprises (i) providing a solution comprising a plurality of silver nanoplates having a plate shape and having a peak optical density between 0.1-10 cm$^{-1}$; (ii) adding a stabilizing agent to the solution; (iii) adding a buffer to the solution; and (iv) concentrating the buffer-containing solution to form a concentrated solution, wherein the concentrated solution comprises a plurality of silver nanoplates having the plate shape, and wherein the concentrated solution has a peak optical density greater than 10 cm$^{-1}$.

In several embodiments, a method for producing a stable, high optical density solution of silver nanoplates comprises the following: (i) adding a stabilizing agent to a solution of silver nanoplates, (ii) adding a buffer (e.g., such as a buffer containing a water soluble salt) to the solution of silver nanoplates, (iii) mixing the stabilizing agent with the buffer and the silver nanoplates over a period of time sufficient for the stabilizing agent to interact with the water soluble salt in the buffer on the surface of the silver nanoplates, and (iv) concentrating the solution to a peak optical density greater than 10 cm$^{-1}$ (e.g., 50-1500 cm$^{-1}$).

The stabilizing agents can include one or more of sodium citrate, a water soluble polymer, (such as polystyrene sodium sulfonate and/or a hydrocarbon polymer derivatized with sulfonate), a poly vinyl based polymer (such as polyvinyl alcohol (PVA) and/or polyvinylpyrrolidone (PVP)), polyethylene glycol, polyacrylic acid, or dextran. The water soluble salt can include one or more of the sulfates, carbonates, chromates, borates, phosphates, and sulfites, acetates, and nitrates. In various embodiments, the combination of the stabilizing agent and a buffer containing one or more water soluble salts provides stabilization to the nanoplate formulation, wherein one of the components of the salt can interact with the stabilizing agent to crosslink the stabilizing agent and increase the stability of a coating on the silver nanoplate. In one embodiment an initial solution of silver nanoplates can be produced from a solution comprising one or more stabilizing agents and a silver source (e.g., such as a silver salt, silver seeds), and in which chemical agents, biological agents, mixing, electromagnetic radiation, and/or heat are used to reduce the silver source (e.g., photoconversion, pH controlled photoconversion, thermal growth, templated growth, and/or seed mediated growth).

In various embodiments, a process for concentrating a solution of silver nanoplates includes the steps of providing a solution comprising a plurality of silver nanoplates having a peak optical density below 10 cm$^{-1}$ (e.g., 0.1-9.9 cm$^{-1}$, 1-9 cm$^{-1}$, 3-7 cm$^{-1}$, 1-5 cm$^{-1}$, and/or 5- 10 cm$^{-1}$), adding a stabilizing agent to the solution, adding a buffer containing a water soluble salt to the solution, and concentrating the solution to a peak optical density greater than 10 cm$^{-1}$ (e.g., 80-150 cm$^{-1}$, 900-1100 cm$^{-1}$, 100 cm$^{-1}$, 1000 cm$^{-1}$ or more). In various embodiments, the peak optical density in increased by 10%, 50%, 100%, 200%, 500%, 1,000%, 10,000% or more, and/or increased by a ratio of 1:1.5, 1:2, 1:5, 1:10 or more, and/or increased by a factor of 1, 1.5, 2, 5, 10, 25, 50, 100, 1000 or more.

In various embodiments, the silver nanoplates have an aspect ratio of between 1.5 and 50 (e.g., 1.5-10, 25-50). In one embodiment, the silver nanoplates comprise an edge length between 10 nm and 300 nm (e.g., 50-250, 65-100 nm). In various embodiments, the stabilizing agent comprises sodium citrate, or at least one water soluble polymer selected from the group consisting of polystyrene sodium sulfonate and a hydrocarbon polymer derivatized with sulfonate. In some embodiments, the water soluble salt comprises one or more of sulfates, carbonates, chromates, borates, phosphates, and sulfites, acetates, and nitrates. In one embodiment, the stabilizing agent comprises at least one of the group consisting of polyvinyl pyrollidone, polyvinyl alcohol, polyethylene glycol, polyacrylic acid, and dextran. In one embodiment, the stabilizing agent comprises a thiol-containing molecule. The thiol-containing molecule can comprise a dihydrolipoic acid or a derivative thereof. The process optionally includes the steps of isolating the concentrated nanoplates and encapsulating the isolated concentrated nanoplates (e.g., with silica or another material). In one embodiment, the process includes the step of concentrating the encapsulated nanoplates to an optical density greater than 10 cm$^{-1}$ (e.g., 100 cm$^{-1}$, 1000 cm$^{-1}$ or more). The stabilizing agent is added prior to the formation of the silver nanoplates. In one embodiment, the nanoplates are concentrated by tangential flow filtration. In one embodiment, the silver concentration is greater than 1.0 mg/mL (e.g., 1-1000, 10-300 mg/mL).

In various embodiments, a process for generating metal oxide coated silver nanoplates is provided. The method can include the steps of providing a solution of silver nanoplates having a peak absorption spectrum between 500 and 1500 nm (e.g., 600-1400, 800-1200 nm) and an optical density greater than 10 cm$^{-1}$ (e.g., 100 cm$^{-1}$, 1000 cm$^{-1}$ or more) and contacting this solution with a solution of metal oxide or metal oxide precursor in an amount sufficient to form a metal oxide coating on an exterior surface of the silver nanoplates. In certain embodiments the silver nanoplates are associated with a stabilizing polymer (e.g., polyvinyl pyrollidone, polyvinyl alcohol, or a combination thereof) prior to contact with the metal oxide precursor, such as by disposing the stabilizing polymer on an exterior surface of the silver nanoplates. In various embodiments, the metal oxide is silica or includes silica.

In various embodiments, a process for generating a solution of silver nanoplates includes the steps of providing a solution comprising a reducing agent, a stabilizing agent, a water soluble polymer, and a silver salt, forming a plurality of silver seeds from the solution, growing the plurality of silver seeds into a plurality of silver nanoplates in the solution to form a silver nanoplate solution, adding a stabilizing agent to the silver nanoplate solution, adding a buffer containing a water soluble salt to the silver nanoplate solution, and concentrating the silver nanoplate solution to a peak optical density greater than 10 cm$^{-1}$ (e.g., 100 cm$^{-1}$, 1000 cm$^{-1}$ or more).

In various embodiments, a composition comprises or consists essentially of a solution of silver nanoplates, wherein the silver nanoplates comprise a poly vinyl polymer. In some embodiments, the poly vinyl polymer comprises polyvinyl pyrollidone or polyvinyl alcohol. In several embodiments, the composition (e.g., solution) comprises one or more salts, such as water soluble salts (e.g., sulfates, carbonates, chromates, borates, phosphates, and sulfites, acetates, and nitrates).

In various embodiments, the poly vinyl polymer is associated with the salt, the poly vinyl polymer coats at least a portion of the silver nanoplates, and/or the poly vinyl polymer is disposed on an exterior surface of the silver nanoplates. In one embodiment, the solution comprises silver nanoplates in a concentration effective to adhere to a non-metal coating material present in the solution. The solution may be formulated to be concentrated. In some embodiments, the optical density of the solution or of the silver nanoplates is greater than 10 cm$^{-1}$ (e.g., 100 cm$^{-1}$, 1000 cm$^{-1}$ or more). The solution may contain a salt (sulfates, carbonates, chromates, borates, phosphates, and sulfites, acetates, and nitrates) at a concentration greater than 0.1 mM (e.g., 0.1 mM to 10 mM). In one embodiment, the solution has a pH greater than 7 (e.g., 8-13). In some embodiments, an absorption spectrum of the silver nanoplates comprises a peak wavelength of between 500 and 1500 nm (e.g., 600-1400, 550-1100, 810-830, 1000-1100 nm). In one embodiment, the solution comprises bicarbonate. The silver nanoplates may be silica-coated. The silver nanoplates can have edge lengths between 10 nm and 500 nm (e.g., 50-300, 100-150 nm).

In various embodiments, a composition comprises or consists essentially of a solution of silver nanoplates bonded to a shell material comprising a poly vinyl polymer. In one embodiment, the silver nanoplates are substantially coated with the poly vinyl polymer. In various embodiments, the composition includes a metal oxide, the metal oxide comprises silica, the poly vinyl polymer comprises polyvinyl alcohol or polyvinylpyrrolidone, the silver nanoplates are bonded to polyvinyl alcohol and silica, and/or the silver nanoplates are bonded to polyvinylpyrrolidone and silica, or any combination thereof. In one embodiment, the composition includes a moiety selected from an amine moiety and a mercapto moiety. In one embodiment, the moiety is bound to the silica. In one embodiment, the composition includes aluminum. In one embodiment, the optical density of the solution is greater than 10 cm$^{-1}$ (e.g., 100-1100 cm$^{-1}$, or more). In one embodiment, the optical density of the silver nanoplates is greater than 10 cm$^{-1}$ (e.g., 100 cm$^{-1}$, 1000 cm$^{-1}$, 11-5000 cm$^{-1}$, or more). In some embodiments, the solution comprises a water soluble salt (such as sulfates, carbonates, chromates, borates, phosphates, and sulfites, acetates, and nitrates) at a concentration greater than 0.1 mM (e.g., 0.5 mM to 2 mM, 0.1 mM to 10 mM). In one embodiment, the pH is greater than 7 (e.g., 8, 9, 10, 11, 12, 13). In one embodiment, the silver nanoplates comprise a peak wavelength of between 500 and 1500 nm (e.g., 700-1300, 810-830, 1000-1100 nm).

In various embodiments, a composition includes silver nanoplates at least partially coated by a shell material that includes a poly vinyl polymer, wherein the mean thickness of the shell material is between 1 nm and 50 nm (e.g., 5, 15, 40 nm). In one embodiment, the silver nanoplates have at least one edge length of between 10 nm and 500 nm. (e.g., 25, 100, 250, 300 nm).

In various embodiments, a kit comprises or consists essentially of one or more containers comprising nanoplates with an optical density greater than 10 cm$^{-1}$ (e.g., 100 cm$^{-1}$, 1000 cm$^{-1}$ or more), a solution suitable for coating nanoplates with a shell of metal oxide, and instructions for use thereof. In one embodiment, the nanoplates comprise a poly vinyl polymer. In one embodiment, the poly vinyl polymer interacts (e.g., cross links or otherwise couples) with the water soluble salt (e.g., sulfates, carbonates, chromates, borates, phosphates, and sulfites, acetates, and nitrates).

In various embodiments, a solution includes silver nanoplates at least partially coated by a silica coating, wherein the silver nanoplates comprise a peak optical density of greater than 10 cm$^{-1}$ (e.g., 11-5000 cm$^{-1}$, 90-1100 cm$^{-1}$, or more). In one embodiment, the silica coating has a shell thickness between 2 and 100 nm (e.g., 10-70, 30-90, 40-60 nm). In one embodiment, the solution comprises a water soluble salt (e.g., sulfates, carbonates, chromates, borates, phosphates, and sulfites, acetates, and nitrates) at a concentration greater than 0.1 mM (e.g., 0.1 mM to 10 mM). In one embodiment, the solution has a pH greater than 7 (e.g., 9, 12, 13). In one embodiment, the silver nanoplates have a peak absorption spectrum comprising a peak wavelength between 500 nm and 1500 nm (e.g., 800-1400 nm). In one embodiment, the silica coating is disposed on an exterior surface of the silver nanoplates. In one embodiment, the coating includes an amine moiety or a mercapto moiety. In one embodiment, the coating further includes aluminum. In one embodiment, the coating includes bicarbonate. In one embodiment, the coating includes polyvinylpyrrolidone. In one embodiment, the silver nanoplates comprise a thickness between 1 nm and 50 nm (e.g., 10-40, 15-25, 5-30). In one embodiment, the silver nanoplates comprise at least one edge length between 10 nm and 500 nm (e.g., 20-400, 50-250, 300-450).

In some embodiments, a process for generating a solution of silver nanoplates with extremely high optical density includes the steps of (i) adding a concentration stabilizing chemical agent to a solution of silver nanoplates or precursor reagents and (ii) increasing the concentration of silver nanoplates to increase the optical density of the solution.

In various embodiments, the silver nanoplates have an aspect ratio of between 1.5 and 25 (e.g., 1.5-10, 1.5-5, 10-30, 25-50); and/or the nanoplate has an edge length between about 10 nm and 250 nm (e.g., 25-180, 50-150 nm); and/or the nanoplate is triangular in cross section; and/or the nanoplate is circular in cross section. In one embodiment, the perimeter of the nanoplate cross section has between 4 and 8 edges (e.g., 5, 6, 7). In various embodiments, the solution of silver nanoplates is formed using one or more of a photoconversion method, a pH-controlled photoconversion method, a thermal growth method, a seed mediated growth method, and/or a solution comprising a shape stabilizing agent or agents and a silver source. In various embodiments, chemical or biological agents, and/or electromagnetic radiation, and/or heat, or a combination thereof are used to reduce the silver source. In one embodiment, the solution of silver nanoplates is formed from some combination of a reducing agent, a shape stabilizing agent, a light source, a heat source, and a silver source.

In one embodiment, an acid, base, or buffer (also termed a "buffering agent") is added to change the solution pH. In various embodiments, the concentration stabilizing chemical agent is added prior to, during, and/or after the formation of the silver nanoplates. In one embodiment, the concentration stabilizing chemical agent acts as a shape stabilizing agent. In one embodiment, the concentration stabilizing chemical agent acts as a reducing agent. In one embodiment, the concentration stabilizing chemical agent acts as an agent to change the solution pH.

In one embodiment, the concentration stabilizing chemical agent is a water soluble polymer. In various embodiments, the polymer is any one or more of a derivative of polysulfonate, sodium polystyrene sulfonate, a derivative of a vinyl polymer, and a polyvinyl alcohol (PVA). In various embodiments, the PVA has a molecular weight of less than about 80,000 Dalton, between about 80,000 Dalton and 120,000 Dalton, and/or more than about 120,000 Dalton. In one embodiment, the polymer is polyvinylpyrrolidone (PVP). In various embodiments, the PVP has a molecular weight of less than about 20,000 Dalton, more than about 20,000 Dalton, between about 20,000 Dalton and 60,000 Dalton, and/or more than about 60,000 Dalton. In one embodiment, the polymer is an ethylene oxide derivative.

In one embodiment, the polymer is a polyethylene glycol (PEG). In various embodiments, the PEG has a molecular weight of less than about 5,000 Dalton, between about 5,000 Dalton and 10000 Dalton, and/or more than about 10000 Dalton. In one embodiment, the PEG contains a single functional group. In one embodiment, the PEG contains two functional groups. According to some embodiments, the functional group or groups consist of one or more of the following: an amine, thiol, acrylate, alkyne, maleimide, silane, azide, hydroxyl, lipid, disulfide, fluorescent molecule, and/or biotin, or combinations thereof. In one embodiment, the functional group or groups can be any one or more of an amine, thiol, acrylate, alkyne, maleimide, silane, azide, hydroxyl, lipid, disulfide, fluorescent molecule, and/or biotin. In one embodiment, the concentration stabilizing agent is a carbohydrate derivative. In various embodiments, the polymer is a monosaccharide, a disaccharide, an oligosaccharide, a polysaccharide, and/or dextran. In various embodiments, the dextran has a molecular weight that is less than about 2000 Dalton (e.g., 500, 1000, 1500 Dalton), between about 2000 Dalton and 5000 Dalton (e.g., 3000, 4000 Dalton), and/or more than about 5000 Dalton (e.g., 6000, 8000, 10000 Dalton or more).

In various embodiments, the concentration stabilizing chemical agent is any one or more of a phenol, a monomeric phenol, a dimeric phenol, a trimeric phenol, a polyphenol, a tannic acid, is gum Arabic, a biological molecule, a protein, a bovine serum albumin, streptavidin, biotin, a peptide, an oligonucleotide, a naturally occurring oligonucleotide, a synthetic oligonucleotide, a metal or metalloid oxide, and/or a silicon dioxide shell. In one embodiment, a silicon dioxide shell has ranges in thickness from about less than 1 nm to about 100 nm (e.g., 2-90, 5-25, 30-70). In one embodiment, a combination of stabilizing agents is used.

In various embodiments, the solvent can be one or more of water, an alcohol, ethanol, isopropyl alcohol, t-butanol, a mixture of a water and an alcohol.

In one embodiment, the concentration of silver nanoplates is increased using tangential flow filtration. In one embodiment, the tangential flow filtration is performed using a tangential flow filter membrane. In one embodiment, the tangential flow membrane is made from a cellulose ester or mix of cellulose esters.

In various embodiments, the tangential flow membrane is made from one or more of polyetheresulfone and/or polysulfone. In various embodiments, the tangential flow membrane has a molecular weight cut off of less than about 10 kD (e.g., 1, 5, 8 kD), of between about 10 kD and 500 kD (e.g., 50, 250, 400 kD), of more than about 500 kD (e.g., 750, 1000, 5000 kD or more), of less than about 0.05 µm (e.g., 0.01, 0.03 µm), of between about 0.05 µm and 0.5 µm (e.g., 0.1, 0.25, 0.4 µm), and/or of more than about 0.5 µm (e.g., 1.0, 2, 5, 10, 100 µm).

In various embodiments, the silver nanoplate solution is concentrated to produce a solution with an optical density of greater than about 10 $cm^{-1}$, greater than about 50 $cm^{-1}$, greater than about 75 $cm^{-1}$, greater than about 100 $cm^{-1}$, and/or greater than about 500 $cm^{-1}$ (e.g., 100-1000, 100-2000 $cm^{-1}$).

In one embodiment, the solvent of the concentrated solution is exchanged using tangential flow filtration. In one embodiment, the concentrated solution is processed to remove residual chemicals using tangential flow filtration.

In various embodiments, a solution of nanoparticles comprising silver nanoparticles is coated with a polymer with an optical density greater than 100 $cm^{-1}$ (e.g., 200, 500, 700, 1500 $cm^{-1}$, or more). In one embodiment, the solution of silver nanoplates is incubated with a substrate. In one embodiment, the substrate is removed from the solution of silver nanoplates and dried.

One embodiment of the present invention provides processes for making solutions of plasmonic nanoparticles, such as e.g., silver nanoplates, that are suitable for performing thermomodulation of a target tissue region. Thermomodulation of a target tissue can be achieved when a composition comprising a plurality of plasmonic nanoparticles is administered to a subject under conditions such that an effective amount of the plasmonic nanoparticles localize to a domain of the target tissue region, and exposing the target tissue region to energy delivered from a excitation surface plasmon resonance source in an amount effective to induce thermomodulation of the domain of the target tissue region. In various embodiments, materials described herein are useful for performing targeted ablative or non-ablative heating of tissue. For example, in one embodiment, provided is a method for performing targeted ablative or non-ablative heating of a tissue to treat a mammalian subject in need thereof, comprising the steps of (i) topically administering to a skin surface of the subject the composition of plasmonic nanoparticles including silver nanoplates; (ii) providing penetration means to redistribute the plasmonic particles from the skin surface to a component of dermal tissue; and (iii) causing irradiation of the skin surface by light.

In several embodiments, the invention comprises compositions that, when used with appropriate methods of administration and excitation with a light-based energy source, can achieve noninvasive or minimally-invasive treatment of skin and underlying tissues, or other accessible tissue spaces with the use of nanoparticles. Use of optical density solutions of plasmonic nanoparticles, such as e.g., silver nanoplates, with short pulse width laser excitation (e.g. pulse widths from 0.1 ms to 1 s) can create steep transient heat gradients that selectively target ablative or non-ablative heat to structures within several cell layers of where particles are localized, e.g. pilosebaceous unit for acne treatment and pore size reduction, targeted epidermal and dermal layers for skin resurfacing and small profile scar remodeling, and hair follicle for permanent hair removal. The treatment can include, but is not limited to, hair removal, hair growth and regrowth, and skin rejuvenation or resurfacing, acne removal or reduction, wrinkle reduction, pore reduction, ablation of cellulite and other dermal lipid depositions, wart and fungus removal, thinning or removal of scars including hypertrophic scars, atrophic scars, and keloids, abnormal pigmentation (such as port wine stains), tattoo removal, and/or skin inconsistencies (e.g. in texture, color, tone, elasticity, hydration). Other therapeutic or preventative methods include, but are not limited to, treatment of hyperhidrosis, anhidrosis, Frey's Syndrome (gustatory sweating), Homer's Syndrome, and Ross Syndrome, actinici keratosis, keratosis follicularis, dermatitis, vitiligo, pityriasis, psoriasis, lichen planus, eczema, alopecia, psoriasis, malignant or non-malignant skin tumors.

BRIEF DESCRIPTION OF THE DRAWINGS

Further objects, features and advantages of the invention(s) will become apparent from the following detailed description taken in conjunction with the accompanying figures showing illustrative embodiments of the invention, in which the following is a description of the drawings. The drawings are examples, and should not be used to limit the embodiments. Moreover, recitation of embodiments having stated features is not intended to exclude other embodiments having additional features or other embodiments incorporating different combinations of the stated features. Further, features in one embodiment (such as in one figure) may be combined with descriptions (and figures) of other embodiments.

DETAILED DESCRIPTION OF THE PREFERRED EMBODIMENT

Figure 1:
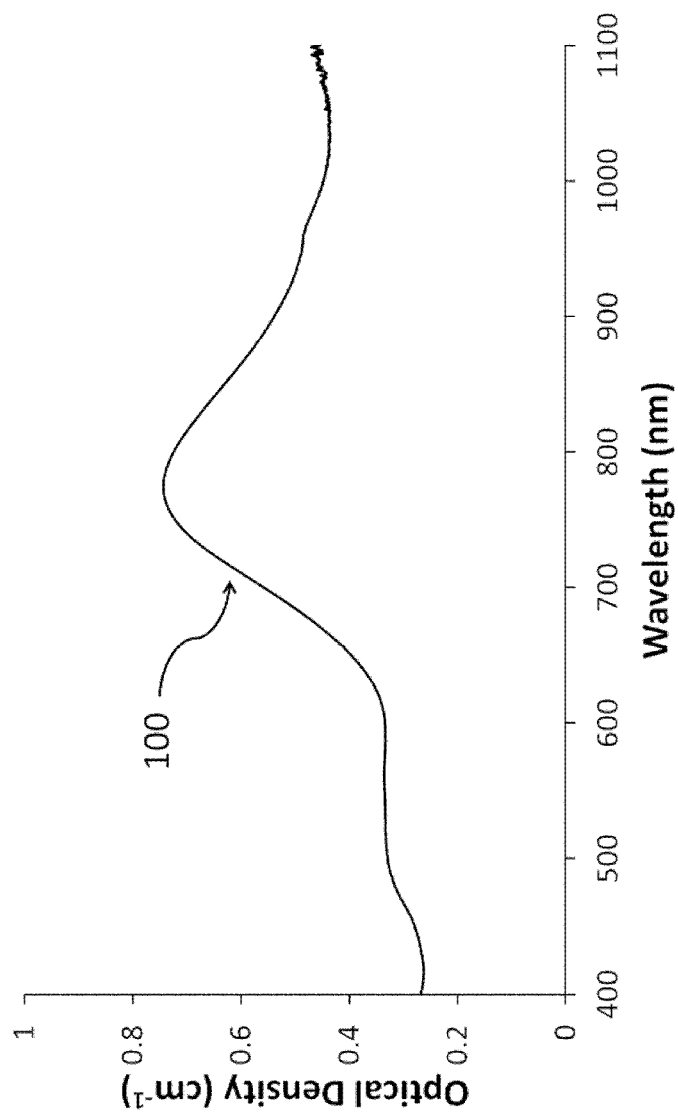
FIG. 1 illustrates the optical spectrum of a silver nanoplate solution fabricated using a photoconversion method according to one embodiment of the present invention. As fabricated, these silver nanoplates, in one embodiment, have a peak optical density of less than 1 cm$^{-1}$ (e.g., approximately 0.8 cm$^{-1}$)

Several embodiments of the present invention comprise processes for making solutions of plasmonic nanoparticle including silver nanoplates that are suitable for performing thermomodulation of a target tissue region. In one embodiment, thermomodulation of a target tissue can be achieved when a composition comprising a plurality of plasmonic nanoparticles is administered to a subject under conditions such that an effective amount of the plasmonic nanoparticles localize to a domain of the target tissue region. The target tissue region is exposed to energy delivered from a excitation surface plasmon resonance source. The energy is delivered in an amount effective to induce thermomodulation of the domain of the target tissue region.

Optical Density (O.D.), which is used herein as a synonym for absorbance, is defined to be the logarithmic ratio of the radiation incident on a material to the radiation transmitted through the material (O.D.=$-\log_{10}(I_1/I_0)$) where $I_1$ is the intensity of transmitted light and $I_0$ is the intensity of the incident light). For solutions, the optical density is a function of the path length through the liquid sample and is expressed in units of cm$^{-1}$. In some instances, optical density is expressed without the unit cm$^{-1}$—such as in instances in which a standard path length of 1 cm is used. In some traditional methods of manufacturing silver nanoplates, the maximum optical density of silver nanoplates in as-synthesized solutions without any additional processing is typically less than 10 cm$^{-1}$ (e.g., 0.1-9.9 cm$^{-1}$, 1-9 cm$^{-1}$, 3-7 cm$^{-1}$, 1-5 cm$^{-1}$, and/or 5-10 cm$^{-1}$). However, according to some embodiments of the present invention, silver nanoplates can be produced with increased optical densities. Generally, optical densities of solutions containing plasmonic particles including silver nanoplates are most effective with an optical density that is higher than 10 cm$^{-1}$ (e.g., 11-5000 cm$^{-1}$, 15-2000 cm$^{-1}$, 20-1000 cm$^{-1}$, 80-150 cm$^{-1}$, 90-110 cm$^{-1}$, 900-1100 cm$^{-1}$, 100 cm$^{-1}$, 1000 cm$^{-1}$ or more) and formulated into a pharmaceutical or cosmetic carrier and stable for days, months, weeks, or years without alterations in particle shape and/or properties. In one embodiment, optical densities of solutions containing plasmonic particles including silver nanoplates are higher than 10 cm$^{-1}$ (e.g., 11-5000 cm$^{-1}$, 15-2000 cm$^{-1}$, 20-1000 cm$^{-1}$, 80-150 cm$^{-1}$, 90-110 cm$^{-1}$, 900-1100 cm$^{-1}$, 100 cm$^{-1}$, 1000 cm$^{-1}$ or more) and formulated into a pharmaceutical or cosmetic carrier and stable for days, months, weeks, or years without alterations in particle shape and/or properties. In one embodiment, the carrier and composition are suitable for topical administration to the skin of a mammalian subject, such that the plasmonic nanoparticles are present in an effective amount for selective thermomodulation of a component of the skin.

In some embodiments, the nanoparticle formulations are formulated for application by a sponge applicator, cloth applicator, direct contact via a hand or gloved hand, spray, aerosol, vacuum suction, high pressure air flow, or high pressure liquid flow, roller, brush, planar surface, semiplanar surface, wax, ultrasound and other sonic forces, mechanical vibrations, hair shaft manipulation (including pulling, massaging), physical force, thermal manipulation, and/or other treatments. In some embodiments, nanoparticle formulation treatments are performed alone, in combination, sequentially or repeated 1-24 times, or more. In other embodiments, the plasmonic nanoparticles are capable of selectively localizing to a first component of the skin, where physical massage or pressure, ultrasound, or heat increase the selective localization of the nanoparticles to this first component. Additionally, the nanoparticles are selectively removable from components of the skin other than the first component, such removal can be accomplished with acetone, alcohol, water, air, peeling of the skin, chemical peeling, waxing, or reduction of the plasmonic compound. Further, in some embodiments the nanoparticles have a coat layer to increase solubility of the nanoparticles in the carrier and/or reduce "stickiness" and accumulation in non-target areas. In one embodiment, at least a portion of an exterior surface of the nanoparticle is modified, such as to include a layer of a polymer, polar monomer, non-polar monomer, biologic compound, a metal (e.g., metallic thin film, metallic composite, metal oxide, or metallic salt), a dielectric, or a semiconductor. In one embodiment, the exterior surface modification is polar, non-polar, charged, ionic, basic, acidic, reactive, hydrophobic, hydrophilic, agonistic, and/or antagonistic. In one embodiment, at least one dimension of at least one nanoparticle within a solution of plasmonic nanoparticles is below 50-100 nm (e.g., 1, 5, 10, 25, 40, 60, 75, 90 nm), and the nanoparticle surface can be coated with a matrix (e.g. silica) of 10-100 nm thickness or more (e.g., 20, 50, 75, 150, 200, 500 nm) in order to increase that dimension or particle to 50-100 nm or more (e.g., 75, 80, 110, 140, 200, 800 nm). This increased dimension size can increase the delivery of all nanoparticles to a target region (e.g., hair follicle, pore, skin, etc.) and limit delivery to non-target region (e.g. dermis).

In various embodiments, materials described herein are useful for performing targeted ablative or non-ablative heating of tissue. For example, in one embodiment, provided is a method for performing targeted ablative or non-ablative heating of a tissue to treat a mammalian subject in need thereof, comprising the steps of (i) topically administering to a skin surface of the subject the composition of plasmonic nanoparticles including silver nanoplates; (ii) providing penetration means to redistribute the plasmonic particles from the skin surface to a component of dermal tissue; and (iii) causing irradiation of the skin surface by light. In further or additional embodiments, provided is a method wherein the light source comprises excitation of mercury, xenon, deuterium, or a metal-halide, phosphorescence, incandescence, luminescence, light emitting diode, or sunlight. In still further or additional embodiments, provided is a method wherein the penetration means comprises high frequency ultrasound, low frequency ultrasound, massage, iontophoresis, high pressure air flow, high pressure liquid flow, vacuum, pre-treatment with fractionated photothermolysis or dermabrasion, or a combination thereof. In still further embodiments, provided is a method wherein the irradiation comprises light having a wavelength of light between about 200 nm and about 10,000 nm (e.g., 300-9000, 700-1300, 800-1200, 800-1300, 900-1100, 550-1100, 810-830, 1000-1100 nm), a fluence of about 1 to about 100 joules/cm$^2$ (e.g., 5-20, 40-70, 10-90), a pulse width of about 1 femtosecond to about 1 second, and a repetition frequency of about 1 Hz to about 1 THz (e.g., 1-10, 10-100, 100-1000, 1000-10000, 10000-100000 Hz or more).

An object of one embodiment of the subject matter described herein is to provide compositions, that when used with appropriate methods of administration and excitation with a light-based energy source can achieve noninvasive and minimally-invasive treatment of skin and underlying tissues, or other accessible tissue spaces with the use of nanoparticles. Use of optical density solutions of plasmonic nanoparticles, such as e.g., silver nanoplates, with short pulse width laser excitation (e.g. pulse widths from 0.1 ms to 1 s) can create steep transient heat gradients that selectively target ablative or non-ablative heat to structures within several cell layers of where particles are localized, e.g. pilosebaceous unit for acne treatment and pore size reduction, targeted epidermal and dermal layers for skin resurfacing and small profile scar remodeling, and hair follicle for permanent hair removal. The treatment can include, but is not limited to, hair removal, hair growth and regrowth, and skin rejuvenation or resurfacing, acne removal or reduction, wrinkle reduction, pore reduction, ablation of cellulite and other dermal lipid depositions, wart and fungus removal, thinning or removal of scars including hypertrophic scars, atrophic scars, and keloids, abnormal pigmentation (such as port wine stains), tattoo removal, and/or skin inconsistencies (e.g. in texture, color, tone, elasticity, hydration). Other therapeutic or preventative methods include, but are not limited to, treatment of hyperhidrosis, anhidrosis, Frey's Syndrome (gustatory sweating), Homer's Syndrome, and Ross Syndrome, actinici keratosis, keratosis follicularis, dermatitis, vitiligo, pityriasis, psoriasis, lichen planus, eczema, alopecia, psoriasis, malignant or non-malignant skin tumors.

Silver Nanoplate Physical Description

In one embodiment, nanoplates, such as silver nanoplates, are characterized by lengths along the three principle axes wherein: the axial length of two of the principle axes is at least two times greater than the axial length of the shortest principle axis, and the shortest principal axial length is less than about 500 nm (e.g., 450. 400, 350, 300, 250, 100, 150, 50, 30, 20, 10 nm). The "edge length" of the nanoplate is defined to be the average of the length of the two longer principle axes. The "thickness" of the nanoplate is defined to be the shortest principal axis.

The ratio of the edge length to the thickness is referred to as the "aspect ratio". In various embodiments the average aspect ratio of the silver nanoplates is greater than 1.5, 2, 3, 4, 5, 7, 10, 20, 30, or 50 and any range therein. In one embodiment the average aspect ratio of the silver nanoplates is between 1.5 and 25, 2 and 25, 1.5 and 50, 2 and 50, 3 and 25, and/or 3 and 50.

In various embodiments a nanoplate has edge lengths less than 500 nm, 250 nm, 200 nm, 150 nm, 100 nm, 80 nm, 60 nm or 50 nm. In one embodiment the nanoplate has edge lengths greater than 5 nm, 10 nm, 20 nm, 30 nm, 50 nm or 100 nm. In various embodiments the edge length is from 30 nm to 100 nm, 20 nm to 150 nm, 10 nm to 200 nm, 10 nm to 300 nm. In various embodiments, the nanoplate has a thickness that is less than 500 nm, 300 nm, 200 nm, 100 nm, 80 nm, 60 nm, 50 nm, 40 nm, 30 nm, 20 nm, and/or 10 nm and any range therein. In various embodiments the nanoplate thickness is from 5 nm to 20 nm, 5 nm to 30 nm, 10 nm to 30 nm, 10 nm to 50 nm, 10 nm to 100 nm.

Various embodiments of silver nanoplates have a variety of different cross sectional shapes including (but not limited to) circular, triangular, or shapes that have any number of discrete edges. In non-limiting embodiments, the nanoplates can be shaped as circular, ovals, squares, rectangles, rods, stars, tubes, pyramids, prisms, triangles, branches, or comprised of a planar surface. In various embodiments the nanoplates have less than 20, 15, 10, 8, 6, 5, or 4 edges, and/or any number between 20 and 1. In various embodiments, the nanoplates can have between 1 and 20, 15, 10, 8, 6, 5, 4, or 3 edges. In one embodiment the nanoplates have more than 2, 3, 4, or 5 edges. In some embodiments the silver nanoplates have sharp corners and in other embodiments the corners are rounded. In some embodiments of silver nanoplates, there are a variety of different cross sectional shapes within the same sample. In other embodiments of silver nanoplate solutions greater than 5%, 10%, 20%, 30%, 40%, 50%, 60%, 70%, 80%, or 90% of the number of particles in solution are silver nanoplates with the other particles having different shapes including but not limited to spherical, cubic, and irregular. In various embodiments, a silver nanoplate solution has a percentage of silver nanoplates, with other particles in the solution having different shapes, including but not limited to spherical, cubic, and/or irregular. In various embodiments, a silver nanoplate solution has 5% to 100%, 10% to 50%, 50% to 100%, 30% to 60%, 60% to 100%, 40% to 70%, 70% to 100%, 50% to 80%, 80% to 100%, 60% to 90%, and/or 90% to 100% of the number of particles in solution are silver nanoplates with the other particles having different shapes including but not limited to spherical, cubic, and/or irregular. In some embodiments, methods can enhance the stability of silver nanoplates to facilitate increased optical density while retaining at least 50%, 60%, 70%, 80%, 90%, 95%, 98% or more of the silver nanoplate shape while undergoing a concentrating process. In some embodiments, methods can enhance the stability of silver nanoplates to facilitate increased optical density while changing shape from the nanoplate to another shape (e.g., spherical, cubic, and/or irregular) in less than 50%, 40%, 30%, 25%, 20%, 10%, 5%, 3,%, 2%, 1% of the silver nanoplates while undergoing a concentrating process. In various embodiments the nanoplates can have one, two, or more flat sides. In another embodiment the nanoplates are pyramidal.

Silver nanoplates have distinct advantages over other plasmonic nanoparticle shapes and compositions. For example, silver nanoplates have advantages over plasmonic nanoparticle shapes and compositions including gold nanoshells and gold nanorods due to potential for lower production costs (less reaction waste and lower material costs). Furthermore, optical density (O.D.) per weight of metal is greater for sliver nanoplates relative to gold nanorods when randomly oriented in solution and irradiated with non-polarized light because the planar surface of a nanoplate resonates with both polarizations of incident light. Additionally, absorbance of silver nanoplates is higher than that of gold nanoshells for the same weight of metal as a greater fraction of light is absorbed versus scattered with a nanoplate architecture relative to a nanoshell. For many applications, these benefits in cost and absorbance can only be realized if nanoplates are stabilized at high concentration and for long periods of time, which is the subject of one embodiment of the present invention.

Silver Nanoplate Fabrication

Modern nanoparticle synthesis techniques have enabled the development of materials with unique optical properties for a wide range of applications including diagnostic, obscurant, and therapeutic applications. Silver nanoplates, as fabricated by current traditional methods including photoconversion, pH controlled photoconversion, thermal growth, and/or seed mediated growth methods typically have optical densities ranging from 0.1 to 10 $cm^{-1}$ (e.g., e.g., 0.1-9.9 $cm^{-1}$, 1-9 $cm^{-1}$, 3-7 $cm^{-1}$, 1-5 $cm^{-1}$, and/or 5-10 $cm^{-1}$). A number of technologies seek higher optical density solutions of silver nanoplates. Several embodiments of the present invention describe a novel and non-obvious method for concentrating silver nanoplates and generating higher optical density silver nanoplate solutions. For example, in various embodiments, methods can increase the optical density of silver nanoplate solutions to greater than 10 $cm^{-1}$, 20 $cm^{-1}$, 30 $cm^{-1}$, 50 $cm^{-1}$, 80 $cm^{-1}$, 100 $cm^{-1}$, 150 $cm^{-1}$, 200 $cm^{-1}$, 300 $cm^{-1}$, 400 $cm^{-1}$, 500 $cm^{-1}$, 600 $cm^{-1}$, 700 $cm^{-1}$, 800 $cm^{-1}$, 900 $cm^{-1}$, and/or 1000 $cm^{-1}$, or more.

Silver nanoplates may be fabricated using photoconversion (Jin et al. 2001; Jin et al. 2003), pH controlled photoconversion (Xue 2007), thermal growth (Hao et al. 2004; Hao 2002; He 2008; Metraux 2005), templated growth (Hao et al. 2004; Hao 2002), seed mediated growth (Aherne 2008; Chen; Carroll 2003; Chen; Carroll 2002, 2004; Chen et al. 2002; He 2008; Le Guevel 2009; Xiong et al. 2007), all herein incorporated by reference, or alternative methods. Alternative methods according to various embodiments of the present invention include methods in which the silver nanoplates are formed from a solution comprising one or more stabilizing agents and a silver source, and in which chemical agents, biological agents, mixing, electromagnetic radiation, and/or heat are used to reduce the silver source.

Figure 2:
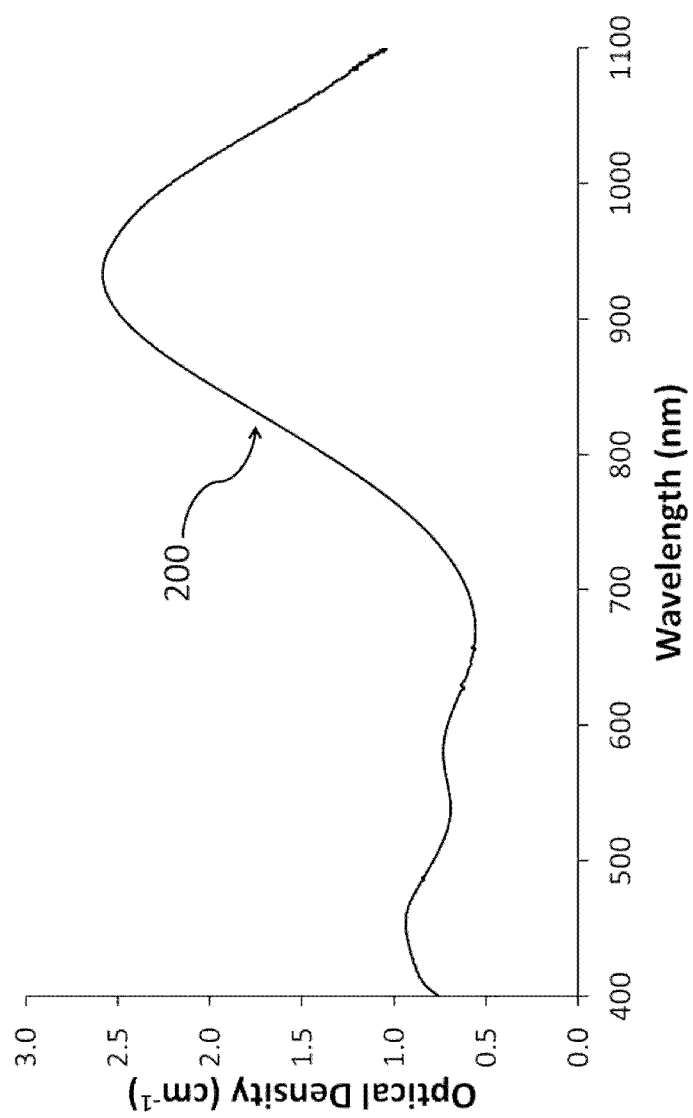
FIG. 2 illustrates the optical spectrum of a silver nanoplate solution fabricated using a seeded growth method according to one embodiment of the present invention. As fabricated, these silver nanoplates have a peak optical density of less than 3 cm$^{-1}$.
Figure 3B:
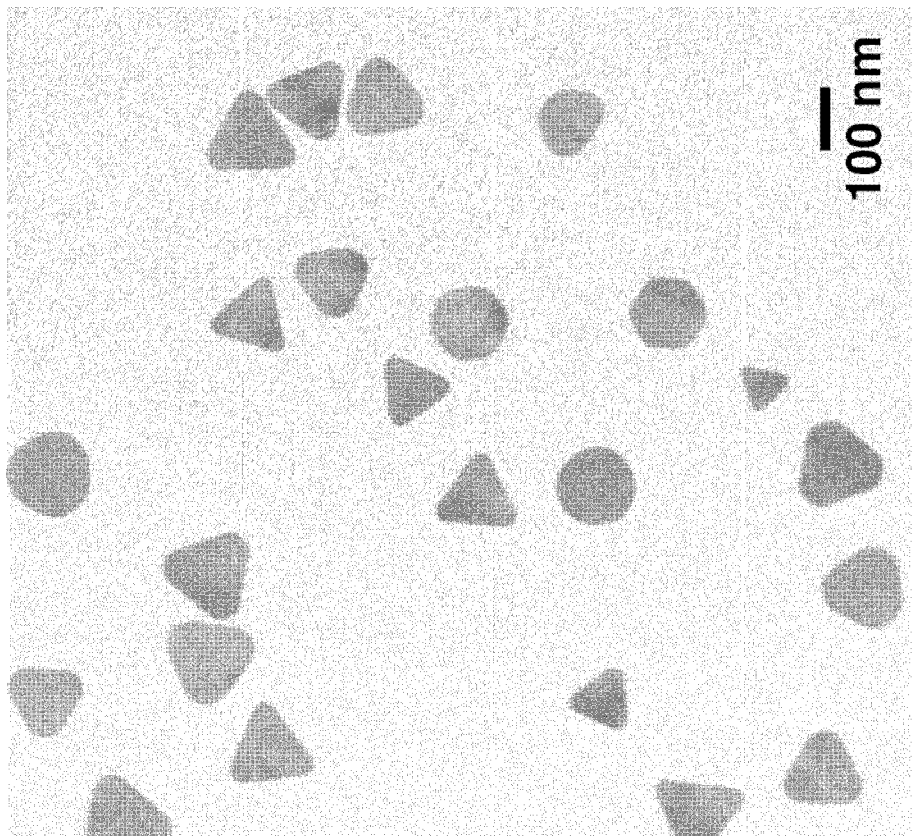
FIG. 3B is a transmission electron microscope image of a silver nanoplate solution fabricated using a seeded growth method according to one embodiment of the present invention.
Figure 3A:
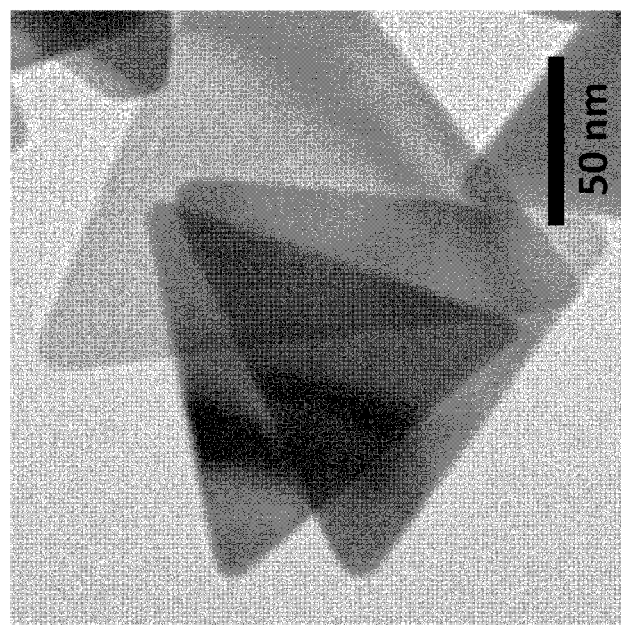
FIG. 3A is a transmission electron microscope image of a silver nanoplate solution fabricated using a photoconversion method according to one embodiment of the present invention.

An optical spectrum of silver nanoplates fabricated using one embodiment of a photoconversion method is shown in FIG. 1. The peak wavelength of the optical spectra (100) is at a wavelength of 775 nm with an optical density of 0.74 $cm^{1}$. The optical spectra of silver nanoplates fabricated using one embodiment of a seed mediated growth method is shown in FIG. 2. The peak wavelength of the optical spectra (200) is at a wavelength of 930 nm with an optical density of 2.58 $cm^{-1}$. A transmission electron microscope image of silver nanoplates made using a photoconversion method is shown in FIG. 3A. A transmission electron microscope image of silver nanoplates made using a seed mediated growth method is shown in FIG. 3B.

Figure 4:
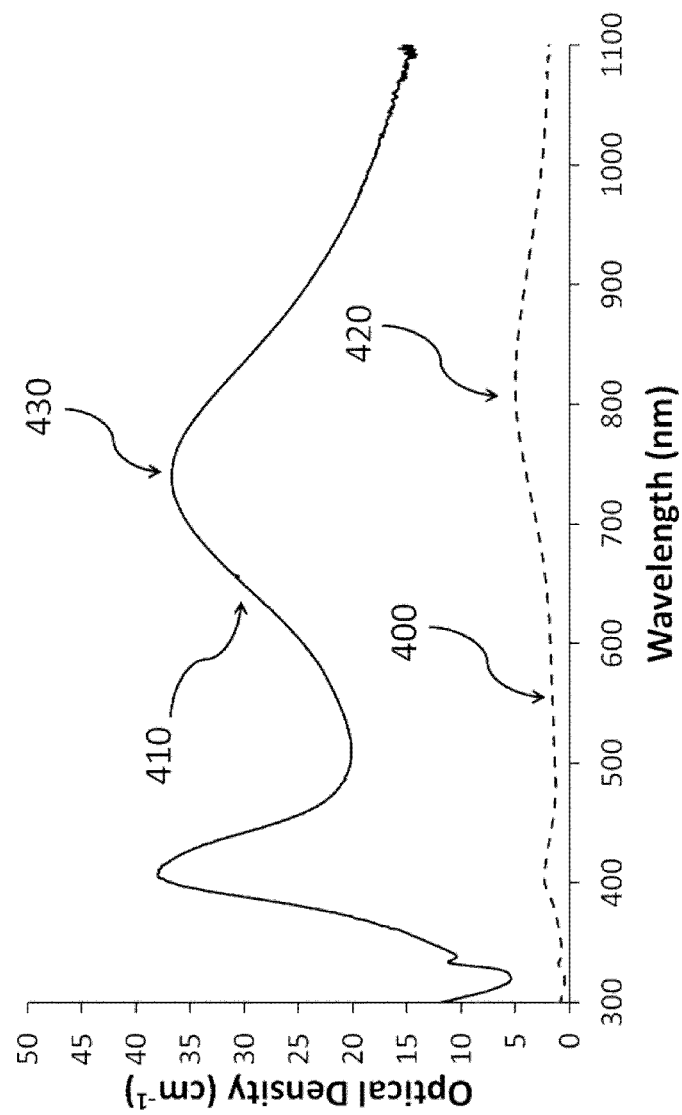
FIG. 4 is the optical spectra of silver nanoplates without the addition of a stabilizing agent and water soluble salt according to one embodiment of the invention before tangential flow concentration and after tangential flow concentration.

In one embodiment, when as-fabricated nanoplates are concentrated using tangential flow filtration, the shape of many of the nanoplates can shift to nanospheres, reducing the formulation efficacy, as evidenced by an increased peak height at .about.400 nm which is the peak optical resonance of spherical silver nanoparticles. FIG. 4 shows the optical density of one embodiment of a solution of the nanoplates in the absence of a concentration stabilization agent before (400) and after (410) concentration. The optical resonance peak that corresponds to the plasmon resonance of the nanoplates shifts from 815 nm (420) to 745 nm (430) demonstrating that the average edge length of the nanoplates is reduced.

Figure 5:
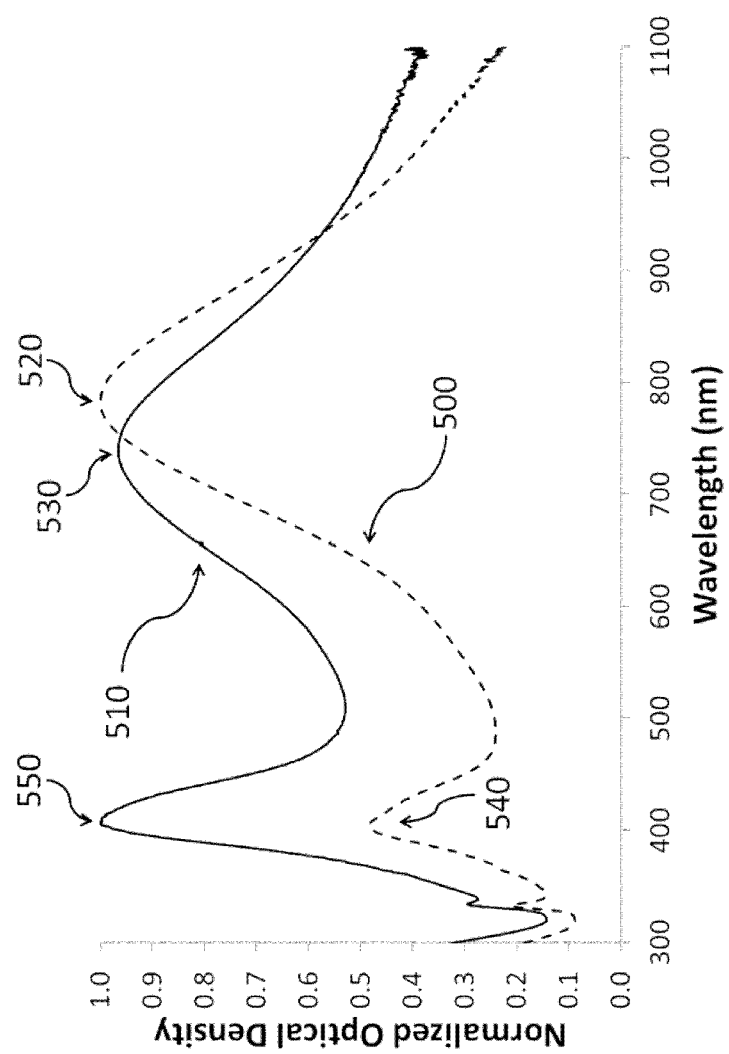
FIG. 5 is the normalized optical spectra of silver nanoplates without the addition of a stabilizing agent and water soluble salt according to one embodiment of the invention before tangential flow concentration and after concentration.

FIG. 5 shows a normalized plot of the nanoplate spectra shown in FIG. 4. For this solution of nanoplates, the intensity of the peak in the 700 nm-850 nm range is correlated to the number of nanoplates in solution. The intensity of the peak in the 400 nm range is correlated to the number of spheroidal particles in solution. Before concentration the ratio of the longer wavelength peak (520) to the shorter wavelength peak (540) is 3. After concentration the ratio of the longer wavelength peak (530) to the shorter wavelength peak (550) is 0.8. This changing ratio demonstrates that the silver nanoplates are changing shape and that the number of nanoplates in solution is reduced.

Figure 6:
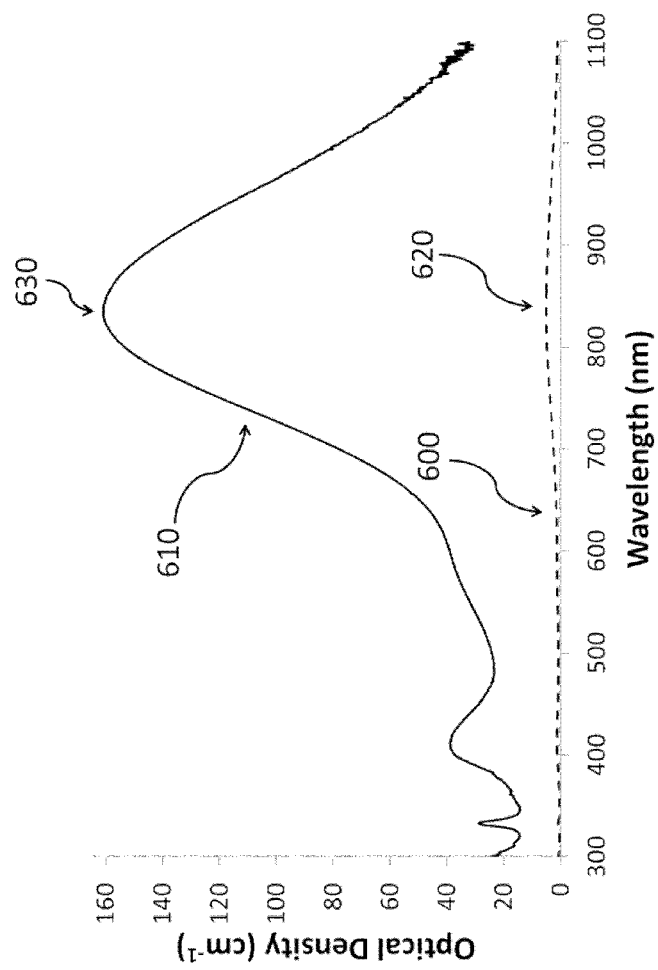
FIG. 6 is the optical spectra according to one embodiment of silver nanoplates combined with polyvinyl alcohol and a water soluble salt before concentration and after concentration.
Figure 7:
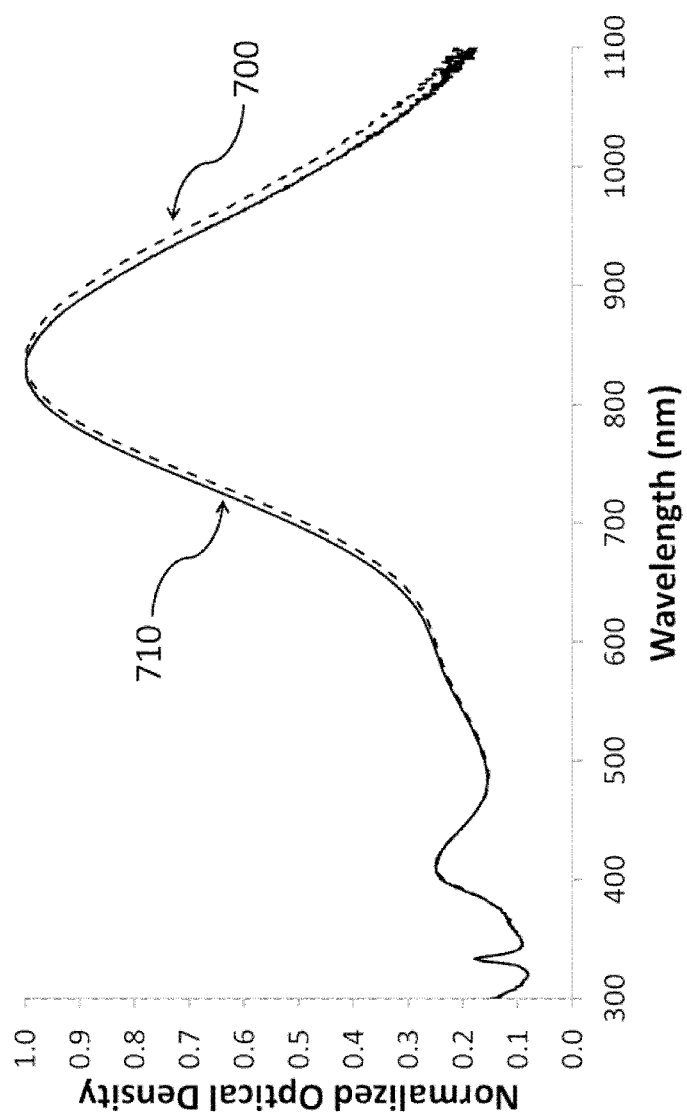
FIG. 7 is the normalized optical spectra according to one embodiment of silver nanoplates combined with polyvinyl alcohol and a water soluble salt before concentration and after concentration.
Figure 8:
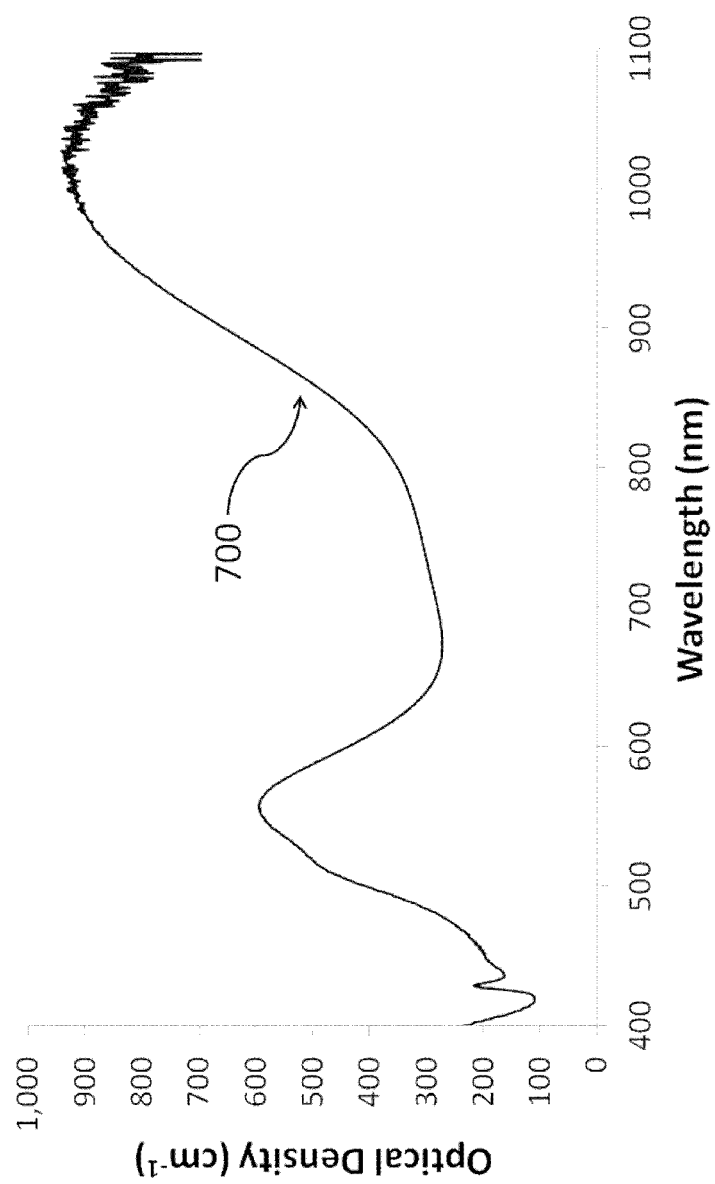
FIG. 8 illustrates an optical extinction spectra of high optical density nanoplate solutions processed using the methods described in various embodiments of the invention.

In one embodiment, a solution of nanoplates can be stabilized. FIG. 6 shows the optical density of one embodiment of a solution of nanoplates that have been stabilized by polyvinyl alcohol in a solution of borate (e.g., sodium borate, potassium tetraborate, etc.). The peak wavelength of the nanoplate peak is the same for both the unconcentrated (620) and concentrated (630) solutions indicating that the edge length of the nanoplates is the same before concentration (600) and after concentration (610). FIG. 7 shows the normalized spectrum which demonstrates that the spectral shape of the peak does not change before concentration (700) and after concentration (710), thereby indicating that in one embodiment, a surface coating is sufficient to prevent the shape of the nanoparticles from shifting. In various embodiments, greater than 10%, greater than 20%, greater than 30% or greater than 50% of the silver nanoplates change shape without a surface protection. In other embodiments less than 20%, less than 10% or less than 5% of the silver nanoplates undergo a shape change if the nanoplates are coated with a protective surface coating. In one embodiment, a spectrum of a nanoplate solution concentrated to have a peak optical density of .about.900 $cm^{-1}$ is shown in FIG. 8.

Figure 9:
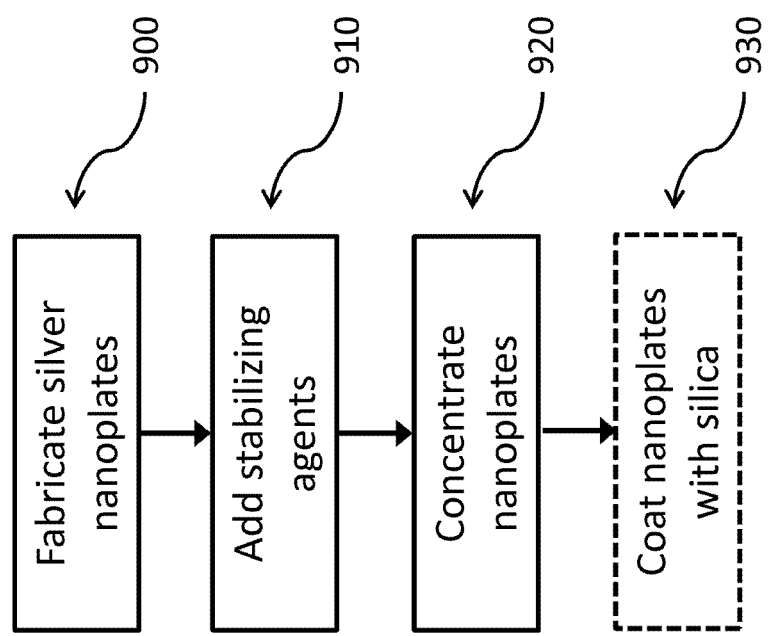
FIG. 9 illustrates steps for producing one embodiment of silver nanoplates by fabricating the silver nanoplates, adding stabilizing agents, concentrating the nanoplates and optionally coating the nanoplates with silica.

In one embodiment, the silver nanoplates are formed in a multi-step process. In one embodiment, the steps to concentrating nanoplates are shown in FIG. 9 and comprise of fabricating the silver nanoplates (900), adding stabilizing agents (910), concentrating the nanoplates (920) and optionally coating the nanoplates with silica (930). In various embodiments, the steps can be taken in any order. In one embodiment, a first step forms silver seeds from an aqueous solution comprising a reducing agent, a stabilizing agent, a water soluble polymer and a silver salt. The reducing agent, stabilizing agent and water soluble polymer may be mixed prior to the addition of a silver source. In various embodiments, the reducing agent used in the silver seed formation step can be formaldehyde, sodium borohydride, another borohydride, hydrogen gas, carbon monoxide gas, hydrazine, or reducing sugars, or combinations of these. In various embodiments, the reducing agent may be present at a concentration of at least 0.1 mM, 1 mM, or 3 mM. In various embodiments the reducing agent may be present at a concentration from 0.1 mM to 1 mM, 0.3 mM to 3 mM, 0.5 mM to 2 mM, 0.1 mM to 2 mM, 0.1 mM to 10 mM.

In various embodiments, the stabilizing agent may be a salt, a polymer, or a biomolecule. In one embodiment the stabilizing agent is trisodium citrate or another citrate derivative.

In one embodiment, the water soluble polymer is a polyanionic polymer including, but not limited to, polymers derivatized with sulfonate, derivatives of polystyrene sulfonate such as an inorganic salt of polystyrene sulfonate, or a monovalent salt of polystyrene sulfonate. In one embodiment the water soluble polymer is poly (sodium styrene sulfonate) (PSSS). In one embodiment the PSSS has a molecular weight between about 3 kDa and about 1,000 kDa. In various embodiments the PSSS has a molecular weight of from 3 kDa to 10 kDa, 5 kDa to 50 kDa, 10 kDa to 100 kDa, 30 kDa to 300 kDa, 50 kDa, to 500 kDa, 100 kDa to 1000 kDa, 300 kDa to 100 kDa, 500 kDa, to 1000 kDa.

In various embodiments, the silver salt may be any water soluble silver salt including but not limited to silver acetate, silver perchlorate, silver nitrate, silver trifluoroacetate, or silver triflate.

In one embodiment, a step for the formulation of silver nanoplates includes having the seeds grown into silver nanoplates in an aqueous solution comprising silver seeds, an acidic reducing agent and a silver salt. In one embodiment, the acidic reducing agent is citric acid or ascorbic acid. The silver salt for the step where seeds are grown into silver nanoplates may be any water soluble silver salt including silver acetate, silver perchlorate, silver nitrate, silver trifluoroacetate, silver triflate, or combinations thereof.

In one embodiment, the silver nanoplates are stirred at a shear flow rate between 1 $s^{-1}$ and 100,000 $s^{-1}$ (e.g., at least 10, 50, 100, 200, 300, 400, 500, 1000, 2000, 5000, 10000, 20000, 50000, 75000, 90000 $s^{-1}$). In various embodiments the silver nanoplates are stirred at a shear flow rate from between 10 $s^{-1}$ and 100 $s^{-1}$, 50 $s^{-1}$ and 500 $s^{-1}$, 100 $s^{-1}$ and 300 $s^{-1}$, 200 $s^{-1}$ and 500 $s^{-1}$, 100 $s^{-1}$ and 400 $s^{-1}$, 500 $s^{-1}$ and 1000 $s^{-1}$, 1000 $s^{-1}$ and 10000 $s^{-1}$, 2000 $s^{-1}$ and 5000 $s^{-1}$, 1000 $s^{-1}$ and 2000 $s^{-1}$, 5000 $s^{-1}$ and/or 10000 $s^{-1}$.

Silver Nanoplate Coating

In one embodiment, silver nanoplates have molecules that are adsorbed or otherwise bound to the particle surface. The molecules on the surface are the reactants or reactant by-products of the synthesis. One object of this invention is to partially or fully exchange the molecules that are bound to the surface of the silver nanoplates with other molecules that more fully protect the particles from changing shape during concentration. Another object of the invention is to use a stabilizing agent during fabrication that generates plate shapes and also stabilizes the plates during subsequent concentration.

In various embodiments, stabilizing agents that may be utilized include chemical or biological agents that are physisorbed (e.g., absorbed by non-molecular binding forces) to the surface, molecularly bound to the surface through specific interactions (e.g. thiol or amine), or encapsulate the surface (e.g. a metal oxide or metalloid oxide shell). In one embodiment, specific chemical agents of interest include polymers. In one embodiment, specific chemical agents of interest include polymers such as polysulfonates. In one preferred embodiment the stabilizing polymer is derivatized with sulfonates. In some embodiments, vinyl polymers, carbohydrates, ethylene oxides, phenols, and carbohydrates may be employed. Specific examples of these polymers include polystyrene sodium sulfonate, polyvinyl alcohol (PVA), polyvinyl pyrrolidone (PVP), polysaccharides, phenol, tannic acid, dextran, and polyethylene glycol (PEG) including PEG molecules which contain one or more chemical groups (e.g. amine, thiol, acrylate, alkyne, maleimide, silane, azide, hydroxyl, lipid, disulfide, fluorescent molecule, or biomolecule moieties). Specific molecules of interest include proteins, peptides, oligonucleotides, biotin, alkane thiols, lipoic and dihydrolipoic acid and derivatives of these acids, bovine serum albumin, streptavidin, neutravidin, wheat germ agglutinin, naturally occurring and synthetic oligonucleotides and peptides, including synthetic oligonucleotides which have one or more chemical functionalities (e.g. amine, thiol, dithiol, acrylic phosphoramidite, azide, digoxigenin, alkynes, or biomolecule moieties). Specific encapsulating chemical agents of interest include metal oxide shells such as $SiO_2$ and $TiO_2$. Stabilizing agents may be added prior to the formation of silver nanoplates, during the formation of silver nanoplates, or after the formation of silver nanoplates. An additional chemical agent of interest is gum arabic. In some embodiments, the stabilizing agent also modifies the pH of the solution.

Carrier Solutions

In one embodiment of this invention, the silver nanoplates are fabricated in aqueous solutions. In other embodiments, the silver nanoplates are fabricated in other solutions that can include ethanol, isopropanol, or organic solvents such as heptane, toluene, or butanol.

In one embodiment an acid, base or buffering agent is added to change the solution pH either before, during, or after the addition of a stabilant. In one embodiment, a buffer, typically containing a water soluble salt, is added. In one embodiment, the water soluble salt comprises borate. In one embodiment, the water soluble salt comprises sodium borate. In one embodiment the nanoplates are suspended in a sodium bicarbonate buffer or a sodium borate buffer. In one embodiment the pH of the solution after addition of the pH modifying agent is greater than pH 6, pH 7, pH 8, pH 9, or pH 10. In various embodiments, the pH of the solution after addition of the pH modifying agent is from pH 6 to pH 8, pH 6.0 to pH 9, pH 7 to pH 10, pH 7 to pH 11, pH 8 to pH 10, pH 8 to pH 11, or pH 7 to pH 12.

In one embodiment, the combination of a nanoplate coating and a water soluble salt present in a buffer provides stabilization to the nanoplate formulation. In some embodiments, one of the components of the salt can interact with the nanoplate coating or stabilizing agent to crosslink the coating and increase the stability of the coating. In various embodiments, such crosslinking can include non-covalent bonds (e.g., ionic bonds, hydrophobic interactions, hydrogen bonds and van der Waals forces including dispersion attractions, dipole-dipole and dipole-induced dipole interactions) and/or covalent bonds between the nanoplate surface, water soluble salts, and/or coating materials/stabilizing agents. In some embodiments the presence of the water-soluble salt present in a buffer changes the binding affinity of a stabilizing agent or coating material to the nanoplate surface, e.g., by modifying the zeta potential and/or charges on the surface of the nanoplate. In other embodiments the water-soluble salt present in a buffer changes the binding affinity of a stabilizing agent or coating material to itself through covalent or non-covalent binding. In some embodiments the presence of the water-soluble salt intermediates binding of a stabilizing agent to the surface of a particle by becoming physisorbed to the particle surface in association with the stabilizing agent. In further embodiments the water-soluble salt intermediates binding of polymer to itself by associating with units of the stabilizing agent or coating materials and lowering the free energy necessary for the coating materials to order on or around a nanoplate surface. In one embodiment, the nanoplate coating is a polymer and the crosslinking produces a viscoelastic gel surrounding all or a portion of the nanoplate. In other embodiments the stabilizing agent is mixed with a buffer containing a water-soluble salt, and both the stabilizing agent and a component of the water soluble salt bind to the surface of the nanoplate. In one embodiment, a polyvinyl based polymer such as polyvinylalcohol or polyvinylpyrrolidone is mixed with a borate salt such as sodium borate. Polyvinylalcohol and borate are can be complexed to form gels via hydrogen bonding (Schultz 1969). In one embodiment, FIG. 6 and FIG. 7 show the effect of stabilizing silver nanoplates with polyvinyl alcohol and sodium borate before concentration to preserve the shape of the nanoparticles.

Surface Stabilization

In various embodiments, stabilizing agents can be solid or liquid formulations that are added to the silver nanoplate solution. The stabilizing agents have an affinity for the surface of the silver nanoplates and are able to associate with the plate surface at wide ranges of relative concentrations. In some embodiments, bound molecules on the silver nanoplates are displaced by a stabilizing agent. Alternatively, a stabilizing agent, such as a polymer, is covalently attached to a silver atom present on the surface of the nanoplate. The polymer coating may extend over all or a portion of the exterior surface of a silver nanoplate. For example, at least 5%, 10%, 15%, 20%, 25%, 50%, 75%, 80%, 90%, 95%, 99%, 99.9% or greater than 99.9% of the exterior surface of a silver nanoplate is coated with one type of polymer or a plurality of different polymer types. In one embodiment, the stabilizing agent is added before the formation of the silver nanoplates while in another embodiment, the stabilizing species is added after the synthesis of the silver nanoplates. Thus, provided are compositions containing polymer-coated silver nanoplates, and solutions containing these compositions may have an optical density less than or equal to 10 $cm^{-1}$. Alternatively, such solutions have polymer-coated silver nanoplates and an optical density greater than 10 $cm^{-1}$; these solutions can be achieved by concentrating or purifying polymer-coated silver nanoplates present in a more dilute solution. In some embodiments the stabilants are added to the as-fabricated silver nanoplate solution. In other embodiments, the solution of nanoplates is washed, or the residual reactants are otherwise removed. In some embodiments, the suspending solution is exchanged one or more times with one or more solution, e.g., to wash the nanoplates or to alter the pH of the solution, before the stabilizing agents are added. Also provided are kits containing, in one or more containers, nanoplates in a solution having an optical density greater than 10 $cm^{-1}$ and a metal oxide-containing solution or a metal oxide precursor-containing suitable for coating the nanoplates with a shell (or coating) of the metal oxide. Preferably, the containers are provided with instructions for use thereof. In some embodiments the kits contain nanoplates having a coating containing a poly vinyl polymer. In other embodiments the poly vinyl polymer contains borate. Nanoplates having a stabilizer coating are characterized as provided herein or otherwise known in the art, such as by particle analyzers or emission detectors such as NMR, Fourier transform spectroscopy, mass spectrometry, or similar assays.

Once the stabilizing agent is added, the mixture of the stabilant and the silver nanoplates can undergo a number of different processes including heating, boiling, boiling under reflux, rotary evaporation, vacuum, stirring, stirring with magnetic stir bars, stirring with overhead mixers, stirring with homogenizers, shaking, microfluidization, refrigeration, and freezing.

Washing and Concentrating

In one embodiment, after the stabilization step is complete, the silver nanoplates can be washed to remove residual reactants or to exchange the solution with another solution. The exchange of solution can be accomplished using dialysis, centrifugation, filtration, or tangential flow filtration (also known as cross flow filtration). In various embodiments, the number of wash volumes exchanged within the sample is zero, 1, 2, 3, 4, 5, 1 and 5, 5 to 10, 10 to 20, or more than 20 wash volumes, inclusive.

Nanoparticle solutions with optical densities greater than 10 $cm^{-1}$ (e.g., 11-5000 $cm^{-1}$, 15-2000 $cm^{-1}$, 20-1000 $cm^{-1}$, 80-150 $cm^{-1}$, 90-110 $cm^{-1}$, 900-1100 $cm^{-1}$, 100 $cm^{-1}$, 1000 $cm^{-1}$ or more) can be fabricated using centrifugation, evaporation, filtration, dialysis or tangential flow filtration. One embodiment of this invention utilizes tangential flow filtration as the process of concentrating the silver nanoplate solution. The filter membrane utilized may be formed from a variety of materials. In various embodiments, specific filter membrane materials of interest can include cellulose esters, polysulfone, and polyetheresulfone. In various embodiments, the filter membrane utilized may have pores with a molecular weight cutoff of less than about 10 kD, between 10 kD to 500 kD, or more than about 500 kD, and/or pore sizes of less than about 0.05 μm, between 0.05 μm and 0.5 μm, or larger than about 0.5 μm. In various embodiments, the filter membrane utilized may have pores with a molecular weight cutoff between 10 kD, to 100 kD, 10 kD to 500 kD, 20 kD to 500 kD, 20 kD to 250 kD and/or pore sizes between 0.02 μm and 0.1 μm, 0.05 μm and 0.2 μm, 0.05 μm and 0.5 μm, 0.10 μm and 0.2 μm, 0.1 μm and 0.5 μm. Tangential flow filtration can also be utilized to change the solvent in which the silver nanoplates are dispersed. In various embodiments, specific solvents of interest include water and alcohols (e.g. t-butanol, ethanol, and isopropyl alcohol), as well as other polar or non-polar solvents. Additionally, tangential flow filtration can be utilized to remove residual chemicals. FIG. 8 shows an embodiment of a solution of nanoplates that has been concentrated to a peak optical absorbance of 930 $cm^{-1}$.

In various embodiments, the silver nanoplate solution concentration is increased to produce a final solution with optical densities of greater than about 5 $cm^{-1}$, greater than about 10 $cm^{-1}$, greater than about 50 $cm^{-1}$, greater than about 75 $cm^{-1}$, greater than about 100 $cm^{-1}$, greater than about 500 $cm^{-1}$, and/or greater than about 1000 $cm^{-1}$. In various embodiments, the silver nanoplate solution concentration is increased to produce a final solution with optical densities from between 10 $cm^{-1}$ to 100 $cm^{-1}$, 30 $cm^{-1}$ to 300 $cm^{-1}$, 50 $cm^{-1}$ to 500 $cm^{-1}$, 100 $cm^{-1}$ to 1000 $cm^{-1}$, 300 $cm^{-1}$ to 3000 $cm^{-1}$, or 500 $cm^{-1}$ to 5000 $cm^{-1}$. One embodiment of the invention is where the silver nanoplate solution concentration is increased to above $10^6$, $10^7$, $10^8$, $10^9$, $10^{10}$, $10^{11}$, $10^{12}$, or, $10^{13}$ particles per milliliter. In various embodiments, the silver nanoplate solution concentration is increased to be between $10^6$ and $10^{13}$, $10^7$ and $10^{13}$, $10^8$ and $10^{13}$, $10^9$ and $10^{13}$, $10^{10}$ and $10^{13}$, $10^{11}$ and $10^{13}$, or $10^{12}$ and $10^{13}$ particles per milliliter. In various embodiments, the silver concentration is greater than 0.1, 1.0, 2, 4, 5, 7, 8, 9, and/or 10 mg/mL. In various embodiments, the silver concentration is between 0.1 to 1.0, 0.3 to 3.0, 0.5 to 5.0, 1.0 to 10.0, 3.0 to 30.0, 5.0 to 50.0, 10.0 to 200.0, 1.0 to 200.0, 1.0 to 500.0, or 10.0 to 500.0 mg/mL.

Silica Coating and Shelling

In one embodiment, the concentrated silver nanoplates are encapsulated with a shell of silica. The coating may extend over all or a portion of the exterior surface of a silver nanoplate. For example, at least 5%, 10%, 15%, 20%, 25%, 50%, 75%, 80%, 90%, 95%, 99%, 99.9% or greater than 99.9% of the exterior surface of a silver nanoplate is coated with silica. The concentrated plates can be mixed with an alcohol (e.g. ethanol or isopropanol). In one embodiment an aminosilane or mercaptosilane is added to the solution to bind silane molecules to the surface of the nanoplates. The binding of silane molecules to the surface of nanoplates is specific to the surface coating on the nanoplates. Some nanoparticle coatings that stabilize the nanoplates during processing will not be compatible with the formation of a silica shell. In one embodiment, the surface of the nanoplates is coated with a molecule that has an affinity for silane molecules in solution. In one embodiment a polyvinyl based polymer such as polyvinylalcohol or polyvinylpyrrolidone is bound to the surface of the nanoplate before the addition of silane molecules. In other embodiments, a polyvinyl based polymer surface is complexed with water soluble salt present in a buffer (e.g., one or more of the sulfates, carbonates, chromates, borates, phosphates, and sulfites, acetates, and nitrates) before the addition of silane molecules. In other embodiments mercaptohexadecanoic acid, mercaptoundecanoic acid, or other thiol containing acids are bound to the surface of the nanoplates. Once there are initial silanes bound to the surface of the nanoplate, additional silane can be added to the solution in the presence of a base to form a silica shell. In one embodiment, the nanoplates coated with a silica shell can be transferred to water and concentrated using a concentration method such as tangential flow filtration. In another embodiment the silica shells are mixed with a solution of aluminum salt such as aluminum chloride, a stabilizing polymer such as polyvinylpyrrolidone, or a buffer such as bicarbonate.

It is an object of this invention to fabricate a solution that comprises a concentrated solution of silver nanoplates coated with a silica shell. In one embodiment, the peak optical density of the solution as measured in a 1 cm path length cuvette is above 10, 20, 50, 100, 500, or 1000. In various embodiments, the peak optical density of the solution as measured in a 1 cm path length cuvette is between 10-100, 20-200, 30-300, 50-500, 100-1000, 200-1000, 300-1000, 500-1000, and/or 200-2000, and any combinations therein. In another embodiment the silver concentration is above 0.1 mg/mL, 1 mg/mL or above 10 mg/mL. In several embodiments the silver concentration is between 0.1 to 1.0, 0.3 to 3.0, 0.5 to 5.0, 1.0 to 10.0, 3.0 to 30.0, 5.0 to 50.0, 10.0 to 200.0, 1.0 to 200.0, 1.0 to 500.0, and/or 10.0 to 500.0 mg/mL, and any combinations therein. In one embodiment, the silica shell thickness is between 2 and 100 nm, and in another embodiment between 5 and 50 nm. In various embodiments, the silica shell thickness is between 3 and 20 nm, 5 and 20 nm, 10 and 20 nm, 10 and 50 nm, 10 and 100 nm, 1 and 10 nm, 3 and 30 nm, 5 and 50 nm, and/or 5 and 200 nm, and any combinations therein. The silica shell can be fabricated from a mixture of silanes including but not limited to aminopropyl triethoxy silane, mercaptopropyl triethoxy silane and tetraethylorthosilicate. The silica shell can contain nitrogen or sulfur atoms. The silica shell can contain amine moieties or mercapto moieties. The silica shell can contain aluminum or sodium atoms.

In another embodiment the solution contains a buffer, that includes a water soluble salt (e.g., one or more of the sulfates, carbonates, chromates, borates, phosphates, and sulfites, acetates, and nitrates) at a concentration greater than 0.1 mM, 1.0 mM or 10.0 mM. In various embodiments the water soluble salt concentration may be from 0.1 mM to 1 mM, 0.3 mM to 3 mM, 0.5 mM to 5 mM, 1 mM to 10 mM, 1 mM to 30 mM, 1 mM to 50 mM, 1 mM to 1000 mM, and any combinations therein. The solution can have a peak absorption wavelength between 500 nm and 1500 nm, 500 nm to 1200 nm, 500 nm to 1000 nm, 600 nm to 1200 nm, 700 nm to 1200 nm, 700 nm to 1500 nm, 700 nm to 900 nm, and/or 900 to 1100 nm, and any combinations therein.

Storage

In various embodiments, the concentrated particles are stored at temperatures below −10, 0, 4, 6, 10, or 20 degrees C. In one embodiment, the particles are frozen and dried under vacuum. In one embodiment, the particles are freeze dried. In one embodiment, the particles are supercritically dried. In one embodiment, an additional stabilant or other cryoprotectant is added to the solution before the particles are heat dried or freeze dried.

Composites

In one embodiment of the invention, high optical density solutions of silver nanoplates are associated with a substrate. In various embodiments, examples of substrates include fibers, cloth, mesh, bandages, socks, wraps, other articles of clothing, sponges, high porosity substrates, particles with edge lengths greater than 1 micron, beads, hair, skin, paper, absorbent polymers, foam, wood, cork, slides, roughened surfaces, biocompatible substrates, filters, or medical implants. In various embodiments, solutions of silver nanoplates at a concentration of at least 1 mg/mL, 10 mg/mL, and/or 100 mg/mL are incubated with the substrate. In several embodiments the silver nanoplate concentration incubated with the substrate is between 0.1 to 1.0, 0.3 to 3.0, 0.5 to 5.0, 1.0 to 10.0, 3.0 to 30.0, 5.0 to 50.0, 10.0 to 20.0, 5.0 to 50.0, 3.0 to 50.0, 1.0 to 100.0 mg/mL, 10.0 to 100.0, 20.0 to 100.0, 30.0 to 100.0 mg/mL. In another embodiment, the solutions of silver nanoplates incubated with the substrate are between $10^6$ and $10^{13}$, $10^7$ and $10^{13}$, $10^8$ and $10^{13}$, $10^9$ and $10^{13}$, $10^{10}$ and $10^{13}$, $10^{11}$ and $10^{13}$, $10^{12}$ and $10^{13}$ or greater than $10^{13}$ particles per milliliter. In another embodiment the silver nanoplates are prepared at an optical density of at least 10, 20, 50, 100, 300, 500, 1000 and/or 2000 cm$^{-1}$ before incubating with the substrate. In various embodiments the silver nanoplates are prepared at an optical density of between 10-100, 20-200, 30-300, 50-500, 100-1000, 200-1000, 300-1000, 500-1000, or 200-2000. In another embodiment the substrate is chemically treated to increase the binding of the nanoplates to the substrate. For example, the substrate could be functionalized with a molecule that yielded a positively or negatively charged surface. In another embodiment, the pH of the incubating solution is selected in order to optimize binding. In another embodiment, the silver nanoplates cover at least 5%, 10%, 20%, 30%, 50% or 75% of the substrate. In various embodiments, the silver nanoplates cover between 5% to 10%, 10% to 100%, 10% to 50%, 50% to 100%, 30% to 100%, 30% to 70%, 40% to 80%, 50% to 90%, 60% to 100%, 70% to 100%, 80% to 100%, 90% to 100%, 0% to 5%, o % to 10%, 0% to 20%, 0% to 30%, or 0% to 50% of the substrate. In another embodiment, other solvents or chemicals are added to the incubation solution. In another embodiment a biological linker (e.g. antibodies, peptides, DNA) is used to bind the high optical density silver nanoplates to the surface of the substrate. In one embodiment, the incubation is for less than 1 minute, 5 minutes, 20 minutes, 60 minutes, or 120 minutes. In various embodiments, the incubation is between 0 to 1 minute, 1 minute to 120 minutes, 5 minutes to 120 minutes, 20 minutes to 120 minutes, 60 minutes to 120 minutes, 5 minutes to 60 minutes, 10 minutes to 60 minutes, 20 minutes to 60 minutes, 0 minutes to 10 minutes, 0 minutes to 20 minutes, or 0 minutes to 5 minutes.

In one embodiment, the substrate is separated from the incubating solution and dried. The substrate can be dried using air drying, heat drying, freeze drying, or supercritical drying. In another embodiment the dried substrate can be further processed by soaking the substrate in another material, painting the substrate with another material, or exposing the substrate to another material that is in the vapor phase.

Other embodiments of the invention will be apparent to those skilled in the art from consideration of the specification and practice of the invention disclosed herein. It is intended that the specification and examples be considered as disclosing certain embodiments of the invention only, with a true scope and spirit of the invention being indicated by the following claims.

The subject matter described herein may be embodied in other specific forms without departing from the spirit or essential characteristics thereof. The foregoing embodiments are therefore to be considered in all respects illustrative rather than limiting. While embodiments are susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited.

The methods disclosed herein include certain actions taken by a practitioner; however, they can also include any third-party instruction of those actions, either expressly or by implication. For example, actions such as "identifying a target region of skin tissue" include "instructing the identification of a target region of skin tissue."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" or "substantially" include the recited numbers. For example, "about 3 mm" includes "3 mm." The terms "approximately", "about" and/or "substantially" as used herein represent an amount or characteristic close to the stated amount or characteristic that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount or characteristic.

EXAMPLES

The description of specific examples below are intended for purposes of illustration only and are not intended to limit the scope of the invention disclosed herein.

Example 1: Silver Nanoplates

Silver nanoplates were synthesized using silver seeds prepared through the reduction of silver nitrate with sodium borohydride in the presence of sodium citrate tribasic and poly sodium styrene sulfonate under aqueous conditions. Silver seed preparation: 21.3 mL of an aqueous 2.5 mM sodium citrate tribasic solution was allowed to mix under magnetic stirring. 1 mL of a 2 g/L poly styrene sodium sulfonate (PSSS) solution was then prepared in a separate beaker. 21.3 mL of a 0.5 mM silver nitrate solution was then prepared by dissolving the salt in water. Once the above solutions have been prepared, 1.33 mL of a 0.5 mM sodium borohydride solution was prepared in 4.degree. C. water. The borohydride and PSSS solutions were then added to the beaker containing the citrate and allowed to mix. The silver nitrate solution was then pumped into the citrate solution using a peristaltic pump at a rate of 100 mL/min. This seed solution was then allowed to stir overnight at room temperature. Silver nanoplates were prepared by mixing 1530 mL Milli-Q water with 35 mL of a 10 mM ascorbic acid solution. Once the solution was sufficiently mixed, the prepared silver seed was added to the reactor. 353 mL of a 2 mM silver nitrate solution was pumped into the reactor at a rate of 100 mL/min. The reaction was mixed for two hours. TEM analysis showed that over 70% of the particles are nanoplates. The optical density of the solution was 2.8 $cm^{-1}$.

Example 2: Concentrated Silver Nanoplates

15 L of silver nanoplates with a peak optical density of about 5 $cm^{-1}$ were mixed with 3.5 g of polyvinylalcohol (PVA) and sodium borate, concentrated using tangential flow filtration using a 500 kD polysulfone tangential flow membrane with 3100 $cm^2$ of surface area. The solution was concentrated for approximately 90 minutes, and the final solution volume was reduced from 15 L to 0.5 L. The silver nanoplate solution optical density was increase to about 150 $cm^{-1}$. Thus, according to one embodiment, a method for increasing a silver nanoplate solution from 5 $cm^{-1}$ to 150 $cm^{-1}$ (e.g., an increase of roughly 30 times the optical density) comprises the steps of adding PVA and sodium borate to silver nanoplates, and concentrating the solution with tangential flow filtration.

Example 3: Concentrated Silver Nanoplates

In one example of concentrating silver nanoplates, 1.2 L of silver nanoplates with a peak optical density of about 4 $cm^{-1}$ were mixed with 4 L of anhydrous ethanol and about 49 mL of ammonium hydroxide solution. 0.6 mL of a dilute aminopropyltriethoxysilane (APTES) was added to the solution. After 15 minutes of incubation, 6.5 mL of tetraethylorthosilicate (TEOS) solution was added. After 24 hours 1 L of the solution was concentrated using a 500 kD polysulfone tangential flow membrane with 1050 $cm^2$ of surface area. The final solution volume was decreased to 150 mL, increasing the silver nanoparticle solution optical density to about 40 $cm^{-1}$. Thus, according to one embodiment, a method for increasing a silver nanoplate solution from 4 $cm^{-1}$ to 40 $cm^{-1}$ (e.g., an increase of roughly 10 times the optical density) comprises the steps of adding anhydrous ethanol, ammonium hydroxide solution, aminopropyltriethoxysilane (APTES), and tetraethylorthosilicate (TEOS) to the silver nanoplates, and concentrating the solution with tangential flow filtration.

Example 4: Nanoplates with a Silica Shell

A silica shell was grown on the surface of 800 nm resonant (.about.75 nm edge length) polyvinylpyrrolidone (PVP) capped silver nanoplates. 400 mL of a solution of 800 nm resonant PVP capped silver nanoplates at a concentration of 2 mg/mL (20 $cm^{-1}$ O.D.) was added to 2.3 L of reagent grade ethanol and 190 mL Milli-Q water under constant stirring. 4.3 mL of dilute aminopropyl triethoxysilane (215 uL APTES in 4.085 mL isopropanol) was then added to the solution, followed immediately by the addition of 44 mL of 30% ammonium hydroxide. After 15 minutes of incubation, 31 mL of dilute tetraethylorthosilicate (1.55 mL TEOS in 29.45 mL isopropanol) was added to the solution. The solution was then left to stir overnight. The nanoplates were then centrifuged on an Ultra centrifuge at 17000 RCF for 15 minutes and reconstituted in Milli-Q water each time and repeated twice. The silica shell thickness was 15 nm. The optical density of the concentrated material was 2040 $cm^{-1}$.

Example 5

A 40 mL solution of 40 O.D. solution of concentrated silver nanoplates stabilized with polyvinylalcohol and sodium borate was spun at 3000 RCF for 30 minutes. The supernatant was removed and the pellet was re-dispersed with bath sonication. The concentrated silver nanoplates had an optical density greater than 900 O.D. as is shown in FIG. 8.

Example 6: Concentrated Nanoplates on a Substrate

A 5 mL solution of 1000 O.D. silver nanoplates was added to a 3"×3" section of absorbent cloth (Absorber Synthetic Drying Chamois, Clean Tools). After addition, the substrate was allowed to air dry. Once dried, the silver nanoplates were bound to the surface of the absorbent cloth and were not released when the cloth was subsequently wet and water removed by applying pressure.

REFERENCES

Aherne, D. L., D. M.; Gara, M.; Kelly, J. M., 2008: Optical Properties and Growth Aspects of Silver Nanoprisms Produced by Highly Reproducible and Rapid Synthesis at Room Temperature. Advanced Materials, 18, 2005-2016.

Chen, S., and D. L. Carroll, 2003: Controlling 2-dimensional growth of silver nanoplates. Self-Assembled Nanostructured Materials Symposium (Mater. Res. Soc. Symposium Proceedings Vol. 775), 343-348|xiii+394.

Chen, S. H., and D. L. Carroll, 2002: Synthesis and characterization of truncated triangular silver nanoplates. Nano Letters, 2, 1003-1007.

Chen, S., and D. L. Carroll, 2004: Silver nanoplates: Size control in two dimensions and formation mechanisms. Journal of Physical Chemistry B, 108, 5500-5506.

Chen, S. H., Z. Y. Fan, and D. L. Carroll, 2002: Silver nanodisks: Synthesis, characterization, and self-assembly. Journal of Physical Chemistry B, 106, 10777-10781.

Hao, E., G. C. Schatz, and J. T. Hupp, 2004: Synthesis and optical properties of anisotropic metal nanoparticles. Journal of Fluorescence, 14, 331-341.

Hao, E. K., K. L.; Hupp, J. T.; Schatz, G. C., 2002: Synthesis of Silver Nanodisks using Polystyrene Mesospheres as Templates. J Am Chem Soc, 124, 15182-15183.

He, X. Z., X.; Chen, Y.; Feng, J., 2008: The evidence for synthesis of truncated silver nanoplates in the presence of CTAB. Materials Characterization, 59, 380-384.

Jin, R., Y. Cao, C. A. Mirkin, K. L. Kelly, G. C. Schatz, and J. G. Zheng, 2001: Photoinduced Conversion of Silver Nanospheres to Nanoprisms. Science, 294, 1901-1903.

Jin, R., Y. C. Cao, E. Hao, G. S. Metraux, G. C. Schatz, and C. A. Mirkin, 2003: Controlling anisotropic nanoparticle growth through plasmon excitation. Nature, 425, 487.

Le Guevel, X. W., F. Y.; Stranik, O.; Nooney, R.; Gubala, V.; McDonagh, C.; MacCraith, B. D., 2009: Synthesis, Stabilization, and Functionalization of Silver Nanoplates for Biosensor Applications. J Phys Chem C, 113, 16380-16386.

Metraux, G. S. M., C. A; 2005: Rapid Thermal Synthesis of Silver Nanoprisms with Chemically Tailorable Thickness. Advanced Materials, 17, 412-415.

Schultz, R. K.; Myers, R. R; 1969: The Chemorheology of Poly(vinyl alcohol)-Borate Gels. Macromolecules, 2, 281-285.

Xiong, Y. J., A. R. Siekkinen, J. G. Wang, Y. D. Yin, M. J. Kim, and Y. N. Xia, 2007: Synthesis of silver nanoplates at high yields by slowing down the polyol reduction of silver nitrate with polyacrylamide. Journal of Materials Chemistry, 17, 2600-2602.

Xue, C. M., C. A., 2007: pH-Switchable Silver Nanoprism Growth Pathways. Angew Chem Int Ed, 46, 2036-2038.

Each of the references listed above is incorporated by reference in its entirety.

What is claimed is:

1. A silver nanoplate solution made by a process comprising the steps of:
   forming a plurality of silver seeds from a solution, wherein the solution comprises a reducing agent, a first stabilizing agent selected from a salt, a polymer, or a biomolecule, and a silver salt;
   growing the plurality of silver seeds into a plurality of silver nanoplates in the solution;
   adding a buffer to the solution comprising the plurality of silver nanoplates;
   adding a second stabilizing agent to the solution comprising the plurality of silver nanoplates, wherein the second stabilizing agent comprises at least one of the group consisting of: an aminopropyltriethoxysilane (APTES), a lipoic acid, a mercaptohexadecanoic acid, a mercaptoundecanoic acid, and a dihydrolipoic acid; and
   concentrating the solution of silver nanoplates until a peak optical density of the solution is greater than about 10 $cm^{-1}$, wherein the silver nanoplate solution comprises concentrated silver nanoplates that preserve shape post-concentration while increasing optical density.

2. The silver nanoplate solution of claim 1, wherein the first stabilizing agent comprises a polymer, polyvinyl pyrollidone, polyvinyl alcohol, polyethylene glycol, dextran, a monosaccharide, a disaccharide, an oligosaccharide, a polysaccharide, a lipoic acid, or a thiol-containing molecule.

3. The silver nanoplate solution of claim 1, wherein the silver nanoplates have at least one of: (a) an aspect ratio of between 1.5 and 50, (2) an edge length between 10 nm and 300 nm, or (3) an absorption spectrum of the silver nanoplates comprises a peak wavelength of between 500 and 1500 nm.

4. The silver nanoplate solution of claim 1, wherein the buffer is a sulfate, carbonate, chromate, borate, phosphate, sulfite, acetate, or nitrate.

5. The silver nanoplate solution of claim 1, wherein the silver nanoplates are functionalized with a functional group or groups selected from one or more of the following: an amine, thiol, acrylate, alkyne, maleimide, silane, azide, hydroxyl, lipid, disulfide, fluorescent molecule, biotin, or combinations thereof.

6. The silver nanoplate solution of claim 5, wherein the process further comprises the steps of:
   isolating the concentrated silver nanoplates; and
   encapsulating the isolated concentrated nanoplates with silica.

7. The silver nanoplate solution of claim 6, further comprising the step of concentrating the encapsulated silver nanoplates to an optical density greater than 100 $cm^{-1}$.

8. The silver nanoplate solution of claim 1, wherein the process further comprises contacting the silver nanoplate solution with a metal oxide in an amount sufficient to form a metal oxide coating on an exterior surface of the silver nanoplates.

9. The silver nanoplate solution of claim 1, wherein the silver nanoplates are coated with a shell having a thickness of between 2 and 100 nm.

10. The silver nanoplate solution of claim 1, wherein the polymer is selected from polystyrene sodium sulfonate, polyvinyl alcohol (PVA), polyvinyl pyrrolidone (PVP), polysaccharides, phenol, tannic acid, dextran, polyethylene glycol (PEG), or PEG molecules that contain one or more chemical groups selected from amine, thiol, acrylate, alkyne, maleimide, silane, azide, hydroxyl, lipid, disulfide, fluorescent molecule, or biomolecule moieties.

11. The silver nanoplate solution of claim 1, wherein the silver nanoplates are functionalized with proteins, peptides, oligonucleotides, biotin, alkane thiols, lipoic and dihydrolipoic acid and derivatives of these acids, bovine serum albumin, streptavidin, neutravidin, wheat germ agglutinin, naturally occurring and synthetic oligonucleotides and peptides, or synthetic oligonucleotides with one or more chemical functional groups selected from amine, thiol, dithiol, acrylic phosphoramidite, azide, digoxigenin, alkynes, or biomolecules.

* * * * *